US006783971B2

(12) United States Patent
Coleman et al.

(10) Patent No.: US 6,783,971 B2
(45) Date of Patent: Aug. 31, 2004

(54) HUMAN GLYCOSYLATION ENZYMES

(75) Inventors: Timothy A. Coleman, Gaithersburg, MD (US); Michael J. Betenbaugh, Baltimore, MD (US)

(73) Assignees: Human Genome Sciences, Inc., Rockville, MD (US); The Johns Hopkins University, Baltimore, MD (US)

( * ) Notice: Subject to any disclaimer, the term of this patent is extended or adjusted under 35 U.S.C. 154(b) by 132 days.

(21) Appl. No.: 09/984,205

(22) Filed: Oct. 29, 2001

(65) Prior Publication Data

US 2002/0137175 A1 Sep. 26, 2002

Related U.S. Application Data

(62) Division of application No. 09/516,143, filed on Mar. 1, 2000, now Pat. No. 6,333,182.
(60) Provisional application No. 60/122,409, filed on Mar. 2, 1999.

(51) Int. Cl.$^7$ .............................. C12N 9/88; C12N 1/20; C12N 15/00; C12N 5/00; C07H 21/04
(52) U.S. Cl. ...................... 435/232; 435/6; 435/252.3; 435/325; 435/320.1; 536/23.2
(58) Field of Search .................... 435/232, 6, 252.3, 435/325, 320.1; 536/23.2

(56) References Cited

U.S. PATENT DOCUMENTS

| | | | |
|---|---|---|---|
| 5,962,302 A | 10/1999 | Hillman et al. | 435/232 |
| 6,030,824 A | 2/2000 | Hillman et al. | 435/232 |

FOREIGN PATENT DOCUMENTS

WO    WO 00/05378    2/2000

OTHER PUBLICATIONS

European Search Report dated Jul. 11, 2002.
European Search Report dated Jun. 10, 2002.
Munster et al., "Mammalian cytidine 5'–monophosphate N–acetylneuraminic acid synthetase: A nuclear protein with evolutionarily conserved structural motifs", Proc. Natl. Acad. Sci. 95:9140–9145 (1998).
XP–002199518; Accession No. 088719; Database SWALL Online!; Nov. 1, 1998.
XP–002199519; Accession No. AJ006215; Database EMBL Online!; Aug. 7, 1998.
Kean, E.L., "Mini Review Sialic Acid Activation", Glycobiology, 1(5):441–447 (1991).
Kolisis, F.N., "Studies on Acylneuraminate Cytidylytransferase from Human Placenta" Archives Internationales de Physiologie et de Biochimie 92:179–184 (1984).
Gu et al., "Improvement of Interferoy–γ Sialylation in Chinese Hamster Ovary Cell Culture by Feeding of N–Acetylmannosamine", Biotechnology and Bioengineering 58(6):642–648 (1998).

Ogonah et al., "Isolation and Characterization of an Insect Cell Line Able to Perform Complex N–Linked Glycosylation on Recombinant Proteins" Biotechnology 14:197–202 (1996).
EMBL/GenBank/DDBJ database Accession No. AJ000855 (Jun. 1, 1998).
Ganguli et al., *Journal of Bacteriology*, 176(15):4583–4589 (1994).
Gilbert et al., *The Journal of Biological Chemistry*, 275(6):3896–3906 (2000).
International Search Report mailed on Aug. 21, 2000, in corresponding International Application No. PCT/US00/05325.
Weikert et al., *Nature Biotechnology*, 17:1116–1121 (1999).
Munster, A–K., et al., "Mammalian cytidin 5'–monophosphate N–acetylneuraminic acid synthetase: A nuclear protein with evolutionarily conserved structural motifs", Proc. Natl. Acad. Sci. USA, vol. 95, pp. 9140–9145 (Aug. 1998).
Redenbach, M., et al., "A set of ordered cosmids and a detailed genetic and physical map for the 8 Mb Streptomyces coelicolor A3(2) chromosome", Mol. Microbiol., vol. 21, No. 1, pp. 77–96 (Jul. 1996).
Genbank Accession No. AI916625 (Dec. 16, 1999).
Genbank Accession No. AI635718 (Dec. 16, 1999).
Genbank Accession No. AI550577 (Mar. 15, 2000).
Genbank Accession No. AI521193 (Apr. 13, 1999).
Genbank Accession No. AI383564 (Mar. 18, 1999).
Genbank Accession No. AI245446 (Nov. 4, 1998).
Genbank Accession No. AI079177 (Sep. 24, 1998).
Genbank Accession No. AA226858 (Feb. 24, 1997).
Genbank Accession No. AA162738 (Dec. 17, 1996).
Genbank Accession No. W79930 (Oct. 17, 1996).
Genbank Accession No. W78156 (Oct. 17, 1996).
Genbank Accession No. N43918 (Feb. 7, 1996).
Genbank Accession No. H65991 (Oct. 18, 1995).
Genbank Accession No. H03606 (Jun. 20, 1995).
Genbank Accession No. R79402 (Jun. 9, 1995).
Genbank Accession No. R24888 (Apr. 20, 1995).
Genbank Accession No. T87365 (Mar. 17, 1995).
Genbank Accession No. T87364 (Mar. 17, 1995).
Genbank Accession No. T78879 (Mar. 15, 1995).
Genbank Accession No. T78878 (Mar. 15, 1995).
Genbank Accession No. AI823915 (Dec. 21, 1999).
Genbank Accession No. AI813508 (Dec. 21, 1999).
Genbank Accession No. AI688701 (Dec. 17, 1999).
Genbank Accession No. AI688690 (Dec. 17, 1999).

(List continued on next page.)

*Primary Examiner*—Maryam Monshipouri
(74) *Attorney, Agent, or Firm*—Human Genome Sciences, Inc.

(57) ABSTRACT

The present invention relates to novel human glycosylation enzyme polypeptides and isolated nucleic acids containing the coding regions of the genes encoding such polypeptides. Also provided are vectors, host cells, antibodies, and recombinant methods for producing human glycosylation enzyme polypeptides. The invention further relates to diagnostic and therapeutic methods useful for diagnosing and treating disorders related to these novel human glycosylation enzyme polypeptides.

118 Claims, No Drawings

OTHER PUBLICATIONS

Genbank Accession No. AI685603 (May 27, 1999).
Genbank Accession No. AI677789 (Dec. 17, 1999).
Genbank Accession No. AI673324 (Dec. 14, 1999).
Genbank Accession No. F36772 (May 13, 1999).
Genbank Accession No. F32570 (May 13, 1999).
Genbank Accession No. F28422 (May 13, 1999).
Genbank Accession No. AI565693 (May 12, 1999).
Genbank Accession No. AI423931 (Mar. 30, 1999).
Genbank Accession No. AI368438 (Feb. 15, 1999).
Genbank Accession No. AI342400 (Feb. 13, 1999).
Genbank Accession No. AI265981 (Jan. 29, 1999).
Genbank Accession No. AI143732 (Nov. 10, 1998).
Genbank Accession No. AI083663 (Nov. 10, 1998).
Genbank Accession No. AI150772 (Oct. 27, 1998).
Genbank Accession No. AI056552 (Sep. 29, 1998).
Genbank Accession No. AI037990 (Sep. 24, 1998).
Genbank Accession No. AI032312 (Aug. 27, 1998).
Genbank Accession No. AI016445 (Aug. 27, 1998).
Genbank Accession No. AI078660 (Apr. 13, 1999).
Genbank Accession No. AA947519 (Jul. 23, 1998).
Genbank Accession No. AA918001 (Jun. 10, 1998).
Genbank Accession No. AA862954 (Apr. 29, 1998).
Genbank Accession No. AA831223 (Mar. 25, 1998).
Genbank Accession No. AA621146 (Mar. 2, 1998).
Genbank Accession No. AA741294 (Feb. 7, 1998).
Genbank Accession No. AA064694 (Dec. 23, 1997).
Genbank Accession No. AA064652 (Dec. 23, 1997).
Genbank Accession No. AA635261 (Nov. 25, 1997).
Genbank Accession No. AA627771 (Oct. 31, 1997).
Genbank Accession No. AA639295 (Oct. 23, 1997).
Genbank Accession No. AA602087 (Oct. 8, 1997).
Genbank Accession No. AA602067 (Oct. 8, 1997).
Genbank Accession No. AA564277 (Sep. 4, 1997).
Genbank Accession No. AA568252 (Aug. 22, 1997).
Genbank Accession No. AA532823 (Aug. 21, 1997).
Genbank Accession No. AA533883 (Aug. 21, 1997).
Genbank Accession No. AA502303 (Aug. 19, 1997).
Genbank Accession No. AA195380 (Apr. 29, 1998).
Genbank Accession No. AA057158 (May 11, 1997).
Genbank Accession No. AA056990 (May 11, 1997).
Genbank Accession No. AA056931 (May 11, 1997).
Genbank Accession No. AA057865 (May 11, 1997).
Genbank Accession No. F20800 (May 17, 1999).
Genbank Accession No. AA373896 (Apr. 21, 1997).
Genbank Accession No. AA325066 (Apr. 20, 1997).
Genbank Accession No. AA308334 (Apr. 18, 1997).
Genbank Accession No. AA270975 (Mar. 26, 1997).
Genbank Accession No. AA121653 (Jan. 30, 1997).
Genbank Accession No. AA133055 (Nov. 27, 1996).
Genbank Accession No. AA132974 (Nov. 27, 1996).
Genbank Accession No. W46683 (Oct. 11, 1996).
Genbank Accession No. W46636 (Oct. 11, 1996).
Genbank Accession No. W05290 (Apr. 23, 1996).
Genbank Accession No. N75480 (Mar. 29, 1996).
Genbank Accession No. N46383 (Feb. 14, 1996).
Genbank Accession No. N37069 (Jan. 16, 1996).
Genbank Accession No. N30051 (Jan. 5, 1996).
Genbank Accession No. N28455 (Jan. 4, 1996).
Genbank Accession No. N27680 (Dec. 30, 1995).
Genbank Accession No. N20843 (Dec. 19, 1995).
Genbank Accession No. H25271 (Jul. 10, 1995).
Genbank Accession No. T82852 (Mar. 16, 1995).
Genbank Accession No. R72258 (Jun. 2, 1995).
Genbank Accession No. AA086111 (Oct. 23, 1996).
Genbank Accession No. AA307074 (Apr. 18, 1997).
Genbank Accession No. AA839024 (Feb. 27, 1998).
Genbank Accession No. AA230788 (Feb. 26, 1997).
Genbank Accession No. C84288 (Mar. 26, 1999).
Genbank Accession No. AA604000 (Oct. 28, 1997).
Genbank Accession No. W85985 (Feb. 2, 1997).
Genbank Accession No. AA032715 (Aug. 22, 1996).
Genbank Accession No. AI701120 (Dec. 18, 1999).
Genbank Accession No. AA981884 (May 27, 1998).
Genbank Accession No. W59582 (Jun. 6, 1996).
Genbank Accession No. AA670706 (Nov. 25, 1997).
Genbank Accession No. AI624434 (Dec. 14, 1999).
Genbank Accession No. T77310 (Mar. 6, 1995).
Genbank Accession No. AA081645 (Oct. 21, 1996).
Genbank Accession No. W65159 (Jun. 10, 1996).
Genbank Accession No. T99986 (Mar. 31, 1995).
Genbank Accession No. AA636878 (Dec. 14, 1995).
Genbank Accession No. H68573 (Oct. 27, 1995).
Genbank Accession No. AA162903 (Feb. 11, 1997).
Genbank Accession No. AI879065 (Aug. 23, 1999).
Genbank Accession No. AA930983 (Apr. 23, 1998).
Genbank Accession No. R74907 (Jul. 25, 1996).
Genbank Accession No. AA792227 (Feb. 9, 1998).
Genbank Accession No. AI888696 (Mar. 8, 2000).
Genbank Accession No. AA417239 (Oct. 16, 1997).
Genbank Accession No. AA384961 (Apr. 21, 1997).
Genbank Accession No. C84527 (Mar. 26, 1999).
Genbank Accession No. AI739429 (Dec. 21, 1999).
Genbank Accession No. AA415331 (Oct. 16, 1997).
Genbank Accession No. R86540 (Aug. 17, 1995).
Genbank Accession No. AI664161 (May 10, 1999).
Genbank Accession No. AA699593 (Dec. 19, 1997).
Genbank Accession No. AA007637 (May 9, 1997).
Genbank Accession No. AI470741 (Mar. 9, 1999).
Genbank Accession No. AA203188 (Jan. 24, 1997).
Genbank Accession No. AI340362 (Feb. 13, 1999).
Genbank Accession No. AA711207 (Dec. 24, 1997).
Genbank Accession No. AA000619 (Jul. 18, 1996).
Genbank Accession No. A778902 (Feb. 5, 1998).
Genbank Accession No. AI117197 (Sep. 2, 1998).
Genbank Accession No. AA475777 (Jun. 18, 1997).
Genbank Accession No. W85750 (Feb. 2, 1997).
Genbank Accession No. AA269909 (Mar. 26, 1997).
Genbank Accession No. AA691227 (Dec. 16, 1997).
Genbank Accession No. AI829102 (Dec. 21, 1999).
Genbank Accession No. AA016640 (Aug. 2, 1996).
Genbank Accession No. AA002459 (Jul. 19, 1996).
Genbank Accession No. AI127768 (Oct. 27, 1998).
Genbank Accession No. AA119079 (Feb. 17, 1997).
Sakakibara et al., Constructions and expression of human aldolase A and B expression plasmids in *Escherichia coli* host, Biochimica et Biophysica Acta, (1989), pp. 334–342.
Lubineau et al., Combined Chemical and Enzymatic Synthesis of the Sialylated Non Reducing Terminal Sequence of $GM_{1b}$ Glycolylated Ganglioside, a Potential Human Tumor Marker, Bioorganic & Medicinal Chemistry, (1994), vol. 2, No. 7, pp. 669–674.

HUMAN GLYCOSYLATION ENZYMES

This application is a divisional of, and claims priority under 35 U.S.C. §120 to, U.S. application Ser. No. 09/516,143, filed on Mar. 1, 2000 (now U.S. Pat. No. 6,333,182, issued Dec. 25, 2001), which is a non-provisional application of, and claims benefit under 35 U.S.C. §119(e), of U.S. Provisional Application No. 60/122,409, filed on Mar. 2, 1999. Each of the above referenced patents and patent applications is hereby incorporated by reference herein in its entirety.

FIELD OF THE INVENTION

The present invention relates to novel human glycosylation enzymes. More specifically, isolated nucleic acid molecules are provided encoding three enzymes involved in post-translational glycosylation: CMP Sialic Acid Synthetase; Sialic Acid Synthetase and Aldolase, collectively "glycosylation enzymes." Amino acid sequences comprising the glycosylation enzymes are also provided. The present invention further relates to methods for treating physiologic and pathologic disease conditions, antibodies, and detection methods.

BACKGROUND OF THE INVENTION

During the last decade, numerous processes and procedures have been developed for genetically engineering cells in order to produce a wide variety of proteins and glycoproteins. These procedures involve utilizing recombinant DNA technology to prepare a vector which includes genetic material that codes for a specific protein or glycoprotein. Upon introduction of the vector into the host cell, the inserted genetic material instructs the host cell's biochemical machinery to manufacture a specific protein or glycoprotein.

Glycoproteins are proteins having carbohydrate groups attached at various points along the protein's amino acid backbone. The carbohydrate groups are commonly attached to asparagine, serine or threonine. The genetic sequence introduced into the host cell usually includes instructions with respect to the amino acid sequence of the protein and the location and structure of the carbohydrate groups. Most of the cell lines which are commonly used as host cells are capable of following the vector's instructions with respect to preparing a protein having a specific amino acid sequence. However, many host cells are not capable of following instructions with respect to glycosylation of the protein. For example, lepidopteran insect cells are a common host cell used in producing a wide variety of proteins in a baculovirus system. However, such lepidopteran cells do not contain all of the cellular glycosylation machinery present in mammalian cells required to attach certain carbohydrate groups to the proteins it manufactures.

From the above, it is apparent that there is a need to identify human polypeptides which can be used to alter the glycosylation machinery of non-human host cells in order to control the structure of carbohydrates attached during glycosylation. Such a process for controlling host cell glycosylation would be useful not only in expressing glycoproteins which accurately mimic naturally occurring proteins, but would also be useful in preparing glycoproteins having selected altered carbohydrate structures for diagnostic and research uses.

SUMMARY OF THE INVENTION

The present invention includes isolated nucleic acid molecules comprising polynucleotides encoding a glycosylation enzyme polypeptide. The present invention further includes glycosylation enzyme polypeptides encoded by these polynucleotides. The present invention further provides for isolated nucleic acid molecules encoding portions (fragments) and/or variants of full length glycosylation enzyme polypeptides and the polypeptides encoded thereby.

Thus, one aspect of the invention provides an isolated nucleic acid molecule comprising a polynucleotide having a nucleotide sequence selected from the group consisting of: (a) a nucleotide sequence encoding a glycosylation enzyme polypeptide having an amino acid sequence as shown in the sequence listing; (b) a nucleotide sequence encoding a mature glycosylation enzyme polypeptide having the amino acid sequences as shown in the sequence listing and described in Table 1; (c) a nucleotide sequence encoding a biologically active fragment of a glycosylation enzyme polypeptide having an amino acid sequence shown in the sequence listing and described in Table 1; (d) a nucleotide sequence encoding an antigenic fragment of a glycosylation enzyme polypeptide having an amino acid sequence shown in the sequence listing and described in Table 1; (e) a nucleotide sequence encoding a glycosylation enzyme polypeptide comprising the complete amino acid sequence encoded by a human cDNA clone contained in the ATCC Deposit and described in Table 1; (f) a nucleotide sequence encoding a mature glycosylation enzyme polypeptide having an amino acid sequence encoded by a human cDNA clones contained in the ATCC Deposit and described in Table 1; (g) a nucleotide squence encoding a biologically active fragment of a glycosylation enzyme polypeptide having an amino acid sequence encoded by a human cDNA clone contained in the ATCC Deposit and described in Table 1; (h) a nucleotide sequence encoding an antigenic fragment of a glycosylation enzyme polypeptide having an amino acid sequence encoded by a human cDNA clone contained in the ATCC Deposit and described in Table 1; and (i) a nucleotide sequence complementary to any of the nucleotide sequences in (a) through (h), above.

Further embodiments of the invention include isolated nucleic acid molecules that comprise, or alternatively consist of, a polynucleotide having a nucleotide sequence at least 80% identical, and more preferably at least 85%, 90%, 95%, 97%, 98% or 99% identical, to any of the nucleotide sequences in (a), (b), (c), (d), (e), (f), (g), (h), or (i) above, or a polynucleotide which hybridizes under stringent hybridization conditions to a polynucleotide in (a), (b), (c), (d), (e), (f), (g), (h), or (i), above. Polypeptides encoded by these nucleic acids or polynucleotides are also encompassed by the invention. In specific embodiments, polynucleotide which hybridizes to a polynucleotide in (a), (b), (c), (d), (e), (f), (g), (h), or (i) above does not hybridize under stringent hybridization conditions to a polynucleotide having a nucleotide sequence consisting of only A residues or of only T residues. An additional nucleic acid embodiment of the invention relates to an isolated nucleic acid molecule comprising, or alternatively consisting of, a polynucleotide which encodes the amino acid sequence of an epitope-bearing portion of a glycosylation enzyme polypeptide having an amino acid sequence in (a), (b), (c), (d), (e), (f), (g), or (h), above. Polypeptides encoded by these nucleic acids are also encompassed by the invention.

The present invention also relates to recombinant vectors, which include the nucleic acid molecules of the present invention, and to host cells containing the recombinant vectors, as well as to methods of making such vectors and host cells and for using them for production of glycosylation enzyme polypeptides or peptides by recombinant techniques. Polypeptides produced by such methods are also provided.

In another embodiment, the invention provides isolated polypeptides comprising a polypeptide having an amino acid sequence described in (a), (b), (c), (d), (e), (f), (g), or (h), above. Polypeptide portions (fragments) or variants of such glycosylation enzyme polypeptides are also provided.

In a specific embodiment, the invention relates to a peptide or polypeptide which comprises or alternatively consists of, the amino acid sequence of an epitope-bearing portion of a glycosylation enzyme polypeptide having an amino acid sequence described above. Peptides or polypeptides having the amino acid sequence of an epitope-bearing portion of a glycosylation enzyme polypeptide of the invention include portions of such polypeptides. In another embodiment, the invention provides an isolated antibody that specifically binds a glycosylation enzyme polypeptide having an amino acid sequence described above.

For a number of applications the level of glycosylation enzyme gene expression can be detected in a sample of tissue or bodily fluid. The presence of glycosylation enzyme gene expression or an increased or decreased level of glycosylation enzyme gene expression can be measured. Thus, the present invention provides for methods useful for detection of glycosylation enzymes and for the diagnosis of applicable disorders. The diagnosis of disorders involves assaying the expression level of the gene encoding the glycosylation enzyme protein in tissue or bodily fluid from an individual and comparing the gene expression level with a standard glycosylation enzyme gene expression level, whereby an increase or decrease in the gene expression level over the standard is indicative of a pathologic disorder.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In the present invention, the sequence identified as SEQ ID NO: 1 was generated by overlapping sequences contained in multiple clones (contig analysis) corresponding to CMP Sialic Acid Synthetase. A representative plasmid containing the sequence for SEQ ID NO: 1 was deposited with the American Type Culture Collection ("ATCC"). The sequence identified as SEQ ID NO:3 was also generated by contig analysis and corresponds to Sialic Acid Synthetase coding sequences. A representative plasmid containing the sequence for SEQ ID NO:3 was deposited with ATCC. Additionally, the sequence identified as SEQ ID NO:5 was generated by contig analysis and corresponds to Aldolase coding sequences. A representative plasmid containing the sequence for SEQ ID NO:5 was deposited with ATCC.

As shown in Table 1, each clone is identified by a cDNA Clone ID (Identifier) and was deposited with the ATCC on Feb. 24, 2000 and assigned ATCC Deposit Number PTA-1410. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

As used herein, a "polynucleotide" refers to a molecule having a nucleic acid sequence contained in SEQ ID NO: 1 (CMP Sialic Acid Synthetase), SEQ ID NO:3 (Sialic Acid Synthetase), or SEQ ID NO:5 (Aldolase) or a human cDNA contained within the plasmid HWLLM34, HA5AA37, or HDPAK85 deposited with the ATCC. For example, the polynucleotide can contain the nucleotide sequence of the full length cDNA sequence, including the 5' and 3' untranslated sequences, the coding region, with or without a natural or artifical signal sequence, the protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

The CMP Sialic Acid Synthetase "polynucleotides" of the present invention also include portions (fragments) or variants of the sequences contained in SEQ ID NO: 1, the complement thereof, or the cDNA within the plasmid deposited with the ATCC, and portions (fragments) or variants of the polynucleotides encoding polypeptides of the invention (for example, polynucleotides encoding a polypeptide comprising or alternatively consisting of SEQ ID NO:2; CMP Sialic Acid Synthetase.) Polynucleotides of the invention also include those polynucleotides capable of hybridizing, under stringent hybridization conditions, to sequences contained in for SEQ ID NO: 1, the complements thereof, or the cDNA within the plasmid deposited with the ATCC.

The Sialic Acid Synthetase "polynucleotides" of the present invention include portions (fragments) or variants of the sequences contained in SEQ ID, NO:3, the complement thereof, or the cDNA within the plasmid deposited with the ATCC, and portions (fragments) or variants of the polynucleotides encoding polypeptides of the invention (for example, polynucleotides encoding a polypeptide comprising or alternatively consisting of SEQ ID NO:4; Sialic Acid Synthetase.) Polynucleotides of the invention also include those polynucleotides capable of hybridizing, under stringent hybridization conditions, to sequences contained in SEQ ID NO:3, the complements thereof, or the cDNA within the plasmid deposited with the ATCC.

The Aldolase "polynucleotides" of the present invention include portions (fragments) or variants of the sequences contained in SEQ ID NO:5, the complement thereof, or the cDNA within the plasmid deposited with the ATCC, and portions (fragments) or variants of the polynucleotides encoding polypeptides of the invention (for example, polynucleotides encoding a polypeptide comprising or alternatively consisting of SEQ ID NO:6; Aldolase.) Polynucleotides of the invention also include those polynucleotides capable of hybridizing, under stringent hybridization conditions, to sequences contained in SEQ ID NO:5, the complements thereof, or the cDNA within the plasmid deposited with the ATCC.

"Stringent hybridization conditions" refers to an overnight incubation at 42° C. in a solution comprising 50% formamide, 5× SSC (750 mM NaCl, 75 mM sodium citrate), 50 mM sodium phosphate (pH 7.6), 5× Denhardt's solution, 10% dextran sulfate, and 20 µg/ml denatured, sheared salmon sperm DNA, followed by washing the filters in 0.1× SSC at about 65° C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6× SSPE (20× SSPE=3M NaCl; 0.2M NaH$_2$PO$_4$; 0.02M EDTA, pH 7.4), 0.5% SDS, 30% formamide, 100 μg/ml salmon sperm blocking DNA; followed by washes at 50° C. with 1× SSPE, 0.1% SDS. In addition, to achieve even lower stringency, washes performed following stringent hybridization can be done at higher salt concentrations (e.g. 5× SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using digo dT as a primer).

CMP Sialic Acid Synthetase, Sialic Acid Synthetase, and/or Aldolase polynucleotides of the present invention can be composed of any polyribonucleotide or polydeoxribonucleotide, which may be unmodified RNA or DNA or modified RNA or DNA. For example, CMP Sialic Acid Synthetase, Sialic Acid Synthetase, and/or Aldolase polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the CMP Sialic Acid Synthetase, Sialic Acid Synthetase, and/or Aldolase polynucleotides can be composed of triple-stranded regions comprising RNA or DNA or both RNA and DNA. A CMP Sialic Acid Synthetase, Sialic Acid Synthetase, and/or Aldolase polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of genomic flanking genes (i.e., 5' or 3' to the CMP Sialic Acid Synthetase, Sialic Acid Synthetase, or Aldolase genes of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

CMP Sialic Acid Synthetase, Sialic Acid Synthetase, and/or Aldolase polypeptides of the present invention can be composed of amino acids joined to each other by peptide bonds or modified peptide bonds, i.e., peptide isosteres, and may contain amino acids other than the 20 gene-encoded amino acids. CMP Sialic Acid Synthetase, Sialic Acid Synthetase, and/or Aldolase polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a CMP Sialic Acid Synthetase, Sialic Acid Synthetase, and/or Aldolase polypeptide, including the peptide backbone, the amino acid side-chains and the amino or carboxyl termini. It will be appreciated that the same type of modification may be present in the same or varying degrees at several sites in a given polypeptide. Also, a given CMP Sialic Acid Synthetase, Sialic Acid Synthetase, and/or Aldolase polypeptide may contain many types of modifications. CMP Sialic Acid Synthetase, Sialic Acid Synthetase, and/or Aldolase polypeptides may be branched, for example, as a result of ubiquitination, and they may be cyclic, with or without branching. Cyclic, branched, and branched cyclic CMP Sialic Acid Synthetase, Sialic Acid Synthetase, and/or Aldolase polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS-STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:1" refers to a CMP Sialic Acid Synthetase polynucleotide sequence while "SEQ ID NO:2" refers to a CMP Sialic Acid Synthetase polypeptide sequence as specified in Table 1.

"SEQ ID NO:3" refers to a Sialic Acid Synthetase polynucleotide sequence while "SEQ ID NO:4" refers to a Sialic Acid Synthetase polypeptide sequence as specified in Table 1.

"SEQ ID NO:5" refers to a Aldolase polynucleotide sequence while "SEQ ID NO:6" refers to a Aldolase polypeptide sequence as specified in Table 1.

Thus, the invention further includes CMP Sialic Acid Synthetase, Sialic Acid Synthetase, and Aldolase polypeptide variants which show functional activity (e.g., biological activity). Such variants include deletions, insertions, inversions, repeats, and substitutions selected according to general rules known in the art so as have little effect on activity.

A CMP Sialic Acid Synthetase, Sialic Acid Synthetase, or Aldolase polypeptide "having biological activity" refers to polypeptides exhibiting activity similar, but not necessarily identical, to CMP Sialic Acid Synthetase, Sialic Acid Synthetase, or Aldolase enzymes of the present invention; including mature forms, as measured in a particular biological assay, with or without dose dependency. In the case where dose dependency does exist, it need not be identical to that of the CMP Sialic Acid Synthetase, Sialic Acid Synthetase, or Aldolase polypeptide, but rather substantially similar to the dose-dependence in a given activity as compared to the to CMP Sialic Acid Synthetase, Sialic Acid Synthetase, or Aldolase polypeptide of the present invention (i.e., the candidate polypeptide will exhibit greater activity or not more than about 25-fold less and, preferably, not more than about tenfold less activity, and most preferably, not more than about three-fold less activity relative to the CMP Sialic Acid Synthetase, Sialic Acid Synthetase, or Aldolase polypeptides of the present invention.)

Polynucleotides and Polypeptides of the Invention

Features of Protein Encoded by Gene No: 1

The translation product of this gene shares significant sequence homology with mouse cytidine 5'-monophosphate N-acetylneuraminic acid synthetase (See Genbank Accession No. AJ006215), which is thought to be important in the glycosylation of polypeptides. Based on the sequence similarity this gene has been termed "cytidine 5'-monophosphate sialic acid synthetase" or "CMP-Sialic Acid Synthetase" herein. Furthermore, based on the sequence similarity the translation product of this gene is expected to share biological activities with mouse cytidine 5'-monophosphate N-acetylneuraminic acid synthetase. Such activities can be assayed using or routinely modifying methods known in the art, such as, for example, those described in Proc. Natl. Acad. Sci. U S A (1998) 95:9140–5, which is incorporated herein by reference in its entirety.

It has been discovered that this gene is expressed primarily in colon tissue, and to a lesser extent in a variety of normal and transformed cell types.

Therefore, polynucleotides and polypeptides of the invention are useful as reagents for differential identification of the tissue(s) or cell type(s) present in a biological sample. Similarly, polypeptides and antibodies directed to these polypeptides are useful to provide immunological probes for differential identification of the tissue(s) or cell type(s). For a number of disorders of the above tissues or cells, particularly of the digestive system, expression of this gene at significantly higher or lower levels may be detected in certain tissues (e.g., colon and cancerous and wounded tissues) or bodily fluids (e.g., lymph, serum, plasma, urine, synovial fluid or spinal fluid) taken from an individual having such a disorder, relative to the standard gene expression level, i.e., the expression level in healthy tissue from an individual not having the disorder.

The homology to mouse cytidine 5'-monophosphate N-acetylneuraminic acid synthetase suggests that polynucleotides and polypeptides corresponding to this gene are useful for treating a disease or condition resulting from the under expression of such a polypeptide in an individual. Polynucleotides and polypeptides corresponding to this gene may be useful for the detection and/or treatment of disorders involving aberrant glycolysis. Disorders involving aberrant glycolysis, resulting from aberrant activity of CMP Sialic Acid Synthetase or any other enzyme involved in the glycolytic pathway, typically manifests itself as cramps, myoglobinuria, or as an intolerance to exercise, or as a fixed, progressive weakness, to name a few. Additionally, polypeptides of the invention and antibodies directed against these polypeptides may be useful, for example, as a tumor marker and/or immunotherapy targets for the above listed tissues.

Features of Protein Encoded by Gene No:2

The translation product of this gene shares significant sequence homology with C. jejuni cytidine sialic acid synthetase (See Genbank Accession No. AJ000855), which is thought to be important in the glycosylation of polypeptides. Based on the sequence similarity this gene has been termed "Sialic Acid Synthetase" herein. Furthermore, based on the sequence similarity the translation product of this gene is expected to share biological activities with C. jejuni cytidine sialic acid synthetase. Such activities can be assayed using or routinely modifying methods known in the art.

The homology to C. jejuni cytidine sialic acid synthetase suggests that polynucleotides and polypeptides corresponding to this gene are useful for treating a disease or condition resulting from the under expression of such a polypeptide in an individual. Polynucleotides and polypeptides corresponding to this gene may be useful for the detection and/or treatment of disorders involving aberrant glycolysis. Disorders involving aberrant glycolysis, resulting from aberrant activity of Sialic Acid Synthetase or any other enzyme involved in the glycolytic pathway, typically manifests itself as cramps, myoglobinuria, or as an intolerance to exercise, or as a fixed, progressive weakness, to name a few. Additionally, polypeptides of the invention and antibodies directed against these polypeptides may be useful, for example, as a tumor marker and/or immunotherapy targets for tissues expressing these polypeptides.

Features of Protein Encoded by Gene No:3

The translation product of this gene shares sequence homology with E. coli N-acylneuraminic acid aldolase (See Nucleic Acids Res. 13 (24), 8843–8852 (1985), incorporated herein by reference), which is a key enzyme used by homofermentative bacteria involved in glycolysis. The end product of this pathway is lactic acid. Members of the heterofermentative bacteria include Streptococcus and Lactococcus, for example. Based on the significant sequence similarity the translation product of this gene has been termed "Aldolase" herein. Furthermore, Aldolase is expected to share biological activity with E. coli N-acylneuraminic acid aldolase which activity can be assayed using or routinely modifying methods known in the art.

It has been discovered that this gene is expressed primarily in immune cells and tissues such as primary dendritic cells, monocytes, and bone marrow, and to a lesser extent in tonsilar tissue, B-cell lymphomas, spleen tissue, spinal cord tissue, and placental tissue.

Therefore, polynucleotides and polypeptides of the invention are useful as reagents for differential identification of the tissue(s) or cell type(s) present in a biological sample and for diagnosis of diseases and conditions, including, but not limited to: muscular disorders involved with aberrant glycolysis, and immune system disorders. Similarly, polypeptides and antibodies directed to these polypeptides are useful to provide immunological probes for differential identification of these tissue(s) or cell type(s). For a number of disorders of the above tissues or cells, particularly of the muscular and immune systems, expression of this gene at significantly higher or lower levels may be detected in certain tissues (e.g., muscular, immune, and cancerous and wounded tissues) or bodily fluids (e.g., lymph, serum, plasma, urine, synovial fluid or spinal fluid) taken from an individual having such a disorder, relative to the standard gene expression level, i.e., the expression level in healthy tissue from an individual not having the disorder.

Given the homology to the *E. coli* aldolase protein, polynucleotides and polypeptides corresponding to this are useful for the detection and/or treatment of disorders involving aberrant glycolysis. Disorders involving aberrant glycolysis, resulting from aberrant activity of aldolase or any other enzyme involved in the glycolytic pathway, typically manifests itself as cramps, myoglobinuria, or as an intolerance to exercise, or as a fixed, progressive weakness, to name a few. Additionally, polypeptides of the invention and antibodies directed against these polypeptides may be useful, for example, as a tumor marker and/or immunotherapy targets for the above listed tissues.

Additionally, each of the polypeptides described above are useful in methods for making humanized proteins, e.g., the method described by Betenbough et al. in U.S. Provisional Patent Application Ser. No. 60/122,582, filed Mar. 2, 1999, and by Betenbough et al. in U.S. Provisional Patent Application Ser. No. 60/169,624, filed Dec. 8, 1999, for expression of exogenous polypeptides in insect cells. U.S. Provisional Patent Application Ser. No. 60/122,582, filed Mar. 2, 1999 and U.S. Provisional Patent Application Ser. No. 60/169,624, filed Dec. 8, 1999 are hereby incorporated herein by reference in entirety. The polypeptides of the invention are responsible for glycosylation of other polypeptides. Such glycosylation is known to result in increased retention of tertiary structure, increased resistance to proteases, half-life in blood, intermolecular interaction, and increased solubility. Many recombinantly produced therapeutically useful proteins are known in the art; e.g., Human Growth Hormone and Alpha Interferon (to name just two), to which such technology could by applied to enhance therapeutic properties of these proteins.

and given ATCC Deposit No: PTA-1410. "Vector" refers to the type of vector contained in the cDNA Clone ID.

"Total NT Seq." refers to the total number of nucleotides in the contig identified by "Gene No." The deposited clone contains all of these sequences, reflected by the nucleotide position indicated as "5' NT of Clone Seq." and the "3' NT of Clone Seq." of SEQ ID NO:X. The nucleotide position of SEQ ID NO:X of the putative methionine start codon (if present) is identified as "5' NT of Start Codon."

The translated amino acid sequence, beginning with the first translated codon of the polynucleodite sequence, is identified as "AA SEQ ID NO:Y," although other reading frames can also be easily translated using known molecular biology techniques. The polypeptides produced by these alternative open reading frames are specifically contemplated by the present invention.

SEQ ID NO:X and the translated SEQ ID NO:Y (where Y may be any of the polypeptide sequences disclosed in the sequence listing) are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited plasmid. These probes will also hybridize to nucleic acid molecules in biological samples, thereby enabling a variety of forensic and diagnostic methods of the invention. Similarly, polypeptides identified from SEQ ID NO:Y may be used to generate antibodies which bind specifically to the proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the

TABLE 1

| Gene No. | cDNA Clone ID | ATCC Deposit No:Z and Date | Vector | NT SEQ ID NO: X | Total NT Seq. | 5' NT of Clone Seq. | 3' NT of Clone Seq. | 5' NT of Start Codon | AA SEQ ID NO: Y | Last AA of ORF |
|---|---|---|---|---|---|---|---|---|---|---|
| 1 | HWLLM34 (CMP Sialic Acid Synthetase) | PTA-1410 Feb. 24, 2000 | pA2 | 1 | 1305 | 1 | 1305 | 1 | 2 | 434 |
| 2 | HA5AA37 (Sialic Acid Synthetase) | PTA-1410 Feb. 24, 2000 | pA2 | 3 | 1080 | 1 | 1080 | 1 | 4 | 359 |
| 3 | HDPAK85 (Aldolase) | PTA-1410 Feb. 24, 2000 | pA2 | 5 | 1429 | 1 | 1429 | 1 | 6 | 230 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID HWLLM34, HA5AA37, and HDPAK85 were deposited with the ATCC on Feb. 24, 2000 generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO: 1, SEQ ID NO:3, and SEQ ID NO:5, and the predicted translated amino acid sequence identified as SEQ ID NO:2, SEQ ID NO:4, and SEQ ID NO:6, respectively, but also a sample of plasmid DNA containing a human cDNA of CMP Sialic Acid Synthetase, Sialic Acid Synthetase, and Aldolase deposited with the ATCC, as set forth in Table 1. The nucleotide sequence of each deposited plasmid can readily be determined by sequencing the deposited plasmid in accordance with known methods. The predicted amino acid sequence can then be verified from such deposits. Moreover, the amino acid sequence of the protein encoded by a particular plasmid can also be directly determined by peptide sequencing or by expressing the protein in a suitable host cell containing the deposited human cDNA, collecting the protein, and determining its sequence.

The present invention also relates to the genes corresponding to SEQ ID NO: 1, SEQ ID NO:2, SEQ ID NO:3, SEQ ID NO:4, SEQ ID NO:5, SEQ ID NO:6, or the deposited clones. The corresponding genes can be isolated in accordance with known methods using the sequence information disclosed herein. Such methods include, but are not limited to, preparing probes or primers from the disclosed sequence and identifying or amplifying the corresponding gene from appropriate sources of genomic material.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to SEQ ID NO:1, 2, 3, 4, 5, 6, or the deposited plasmids, using information from the sequences disclosed herein or the plasmids deposited with the ATCC. For example, allelic variants and/or species homologs may be isolated and identified by making suitable probes or primers from the sequences provided herein and screening a suitable nucleic acid source for allelic variants and/or the desired homologue.

The CMP Sialic Acid Synthetase, Sialic Acid Synthetase, and/or Aldolase polypeptides of the invention can be prepared in any suitable manner. Such CMP Sialic Acid Synthetase, Sialic Acid Synthetase, and/or Aldolase polypeptides include isolated naturally occurring polypeptides, recombinantly produced polypeptides, synthetically produced polypeptides, or polypeptides produced by a combination of these methods. Means for preparing such polypeptides are well understood in the art.

The CMP Sialic Acid Synthetase, Sialic Acid Synthetase, and/or Aldolase polypeptides may be in the mature form, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The CMP Sialic Acid Synthetase, Sialic Acid Synthetase, and/or Aldolase polypeptides of the present invention are preferably provided in an isolated form, and preferably are substantially purified. A recombinantly produced version of a polypeptide, including the secreted polypeptide, can be substantially purified using techniques known in the art, such as, for example, the one-step method described in Smith and Johnson, Gene 67:31–40 (1988). In specific embodiments, CMP Sialic Acid Synthetase, Sialic Acid Synthetase, and/or Aldolase polypeptides of the invention are purified from natural or recombinant sources using antibodies of the invention raised against CMP Sialic Acid Synthetase, Sialic Acid Synthetase, or Aldolase proteins using methods which are well known in the art.

The present invention provides polynucleotides comprising, or alternatively consisting of, the nucleic acid sequences of SEQ ID NO:1, SEQ ID NO:3, SEQ ID NO:5 and/or a cDNA contained in the ATCC deposit. The present invention also provides polypeptides comprising, or alternatively, consisting of, the polypeptide sequences of SEQ ID NO:2, SEQ ID NO:4, SEQ ID NO:6, and/or a polypeptide encoded by a cDNA contained in the ATCC deposit. Polynucleotides encoding a polypeptide comprising, or alternatively consisting of the polypeptide sequence of SEQ ID NO:2, SEQ ID NO:4, SEQ ID NO:6, and/or a polypeptide sequence encoded by a cDNA contained in the ATCC deposit are also encompassed by the invention.

The following procedures can be used to obtain full length genes or full length coding portions of glycosylation enzyme genes using the information from the sequences disclosed herein or the clones deposited with the ATCC.

Procedure 1

RACE Protocol For Recovery of Full-length Genes

Partial cDNA clones can be made full-length by utilizing the rapid amplification of cDNA ends (RACE) procedure described in Frohman et al. Proc. Nat'l. Acad. Sci. USA, 85:8998–9002 (1988). A cDNA clone missing either the 5' or 3' end can be reconstructed to include the absent base pairs extending to the translational start or stop codon, respectively. In some cases, cDNAs are missing the start of translation, therefor. The following briefly describes a modification of this original 5' RACE procedure. Poly A+ or total RNA is reverse transcribed with Superscript II (Gibco/BRL) and an antisense or complementary primer specific to the cDNA sequence. The primer is removed from the reaction with a Microcon Concentrator (Amicon). The first-strand cDNA is then tailed with dATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoI, SalI and ClaI) at the 5' end and a primer containing just these restriction sites. This double-stranded cDNA is PCR amplified for 40 cycles with the same primers as well as a nested cDNA-specific antisense primer. The PCR products are size-separated on an ethidium bromide-agarose gel and the region of gel containing cDNA products the predicted size of missing protein-coding DNA is removed. cDNA is purified from the agarose with the Magic PCR Prep kit (Promega), restriction digested with XhoI or SalI, and ligated to a plasmid such as pBluescript SKII (Stratagene) at XhoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone. Similar methods known in the art and/or commercial kits are used to amplify and recover 3' ends.

Several quality-controlled kits are available for purchase. Similar reagents and methods to those above are supplied in kit form from Gibco/BRL for both 5' and 3' RACE for recovery of full length genes. A second kit is available from Clontech which is a modification of a related technique, SLIC (single-stranded ligation to single-stranded cDNA), developed by Dumas et al. (Dumas et al., Nucleic Acids Res., 19:5227–5232 (1991)). The major differences in procedure are that the RNA is alkaline hydrolyzed after reverse transcription and RNA ligase is used to join a restriction site-containing anchor primer to the first-strand cDNA. This obviates the necessity for the dA-tailing reaction which results in a polyT stretch that is difficult to sequence past.

An alternative to generating 5' or 3' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

RNA Ligase Protocol For Generating The 5' or 3' End Sequences To Obtain Full Length Genes Once a gene of interest is identified, several methods are available for the identification of the 5' or 3' portions of the gene which may not be present in the original cDNA clone. These methods include but are not limited to filter probing, clone enrichment using specific probes and protocols similar and identical to 5' and 3' RACE. While the full length gene may be present in the library and can be identified by probing, a useful method for generating the 5' or 3' end is to use the existing sequence information from the original cDNA to generate the missing information. A method similar to 5' RACE is available for generating the missing 5' end of a desired full-length gene. (This method was published by Fromont-Racine et al., Nucleic Acids Res., 21(7): 1683–1684 (1993). Briefly, a specific RNA oligonucleotide is ligated to the 5' ends of a population of RNA presumably containing full-length gene RNA transcript and a primer set containing a primer specific to the ligated RNA oligonucleotide and a primer specific to a known sequence of the gene of interest, is used to PCR amplify the 5' portion of the desired full length gene which may then be sequenced and used to generate the full length gene. This method starts with total RNA isolated from the desired source, poly A RNA may be used but is not a prerequisite for this procedure. The RNA preparation may then be treated with phosphatase if necessary to eliminate 5' phosphate groups on degraded or damaged RNA which may interfere with the later RNA ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase. This modified RNA preparation can then be used as a template for first strand cDNA synthesis using a gene specific oligonucleotide. The first strand synthesis reaction can then be used as a template for PCR amplification of the desired 5' end using a primer specific to the ligated RNA oligonucleotide and a primer specific to the known sequence of the glycosylation enzyme gene of interest. The resultant product is then sequenced and analyzed to confirm that the 5' end sequence belongs to the glycosylation enzyme gene.

Polynucleotide and Polypeptide Fragments

The present invention is further directed to nucleic acid molecules encoding portions or fragments of the polynucleotide sequences described herein, e.g., shown in the sequence listing or contained in the deposited clones. Uses for the polynucleotide fragments of the present invention include, but are not limited to, probes, primers, molecular weight, markers and for expressing the polypeptide fragments of the present invention. Fragments include portions of the polynucleotide sequences, at least 10 contiguous nucleotides in length selected from any two integers, one of which representing a 5' nucleotide position and a second of which representing a 3' nucleotide position, where the first, or 5' most, nucleotide for each disclosed polynucleotide sequence is position 1. That is, every combination of a 5' and 3' nucleotide position that a fragment at least 10 contiguous nucleotides in length could occupy is included in the invention as an individual specie. "At least" means a fragment may be 10 contiguous nucleotide bases in length or any integer between 10 and the length of an entire nucleotide sequence minus 1. Therefore, included in the invention are contiguous fragments specified by any 5' and 3' nucleotide base positions of a polynucleotide sequences wherein the contiguous fragment is any integer between 10 and the length of an entire nucleotide sequence minus 1. The polynucleotide fragments specified by 5' and 3' positions can be immediately envisaged using the clone description and are therefore not individually listed solely for the purpose of not unnecessarily lengthening the specifications. Although it is particularly pointed out that each of the above described species are included in the present invention.

Further, the invention includes polynucleotides comprising sub-genuses of fragments specified by size, in nucleotides, rather than by nucleotide positions. The invention includes any fragment size, in contiguous nucleotides, selected from integers between 10 and the length of an entire nucleotide sequence minus 1 (where 1 is the first, or 5' most, nucleotide for each disclosed polynucleotide sequence). Preferred sizes of contiguous nucleotide fragments include 20 nucleotides, 30 nucleotides, 40 nucleotides, 50 nucleotides, 60 nucleotides, 70 nucleotides, 80 nucleotides, 90 nucleotides, 100 nucleotides, 125 nucleotides, 150 nucleotides, 175 nucleotides, 200 nucleotides, 250 nucleotides, 300 nucleotides, 350 nucleotides, 400 nucleotides, 450 nucleotides, 500 nucleotides, 550 nucleotides, 600 nucleotides, 650 nucleotides, 700 nucleotides, 750 nucleotides, 800 nucleotides, 850 nucleotides, 900 nucleotides, 950 nucleotides, 1000 nucleotides. Other preferred sizes of contiguous polynucleotide fragments, which may be useful as diagnostic probes and primers, include fragments 50–300 nucleotides in length which include, as discussed above, fragment sizes representing each integer between 50–300. Larger fragments are also useful according to the present invention corresponding to most, if not all, of the polynucleotide sequences of the sequence listing or deposited clones. The preferred sizes are, of course, meant to exemplify not limit the present invention as all size fragments, representing any integer between 10 and the length of an entire nucleotide sequence minus 1 of the sequence listing or deposited clones, are included in the invention. Additional preferred nucleic acid fragments of the present invention include nucleic acid molecules encoding epitope-bearing portions of the polypeptides.

Moreover, representative examples of polynucleotide fragments of the invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, or 1251 to the end of SEQ ID NO: 1, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Polynucleotides which hybridize to these nucleic acid molecules under stringent hybridization conditions or lower stringency conditions are also encompassed by the invention, as are polypeptides encoded by these polynucleotides.

Additionally, representative examples of polynucleotide fragments of the invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, or 1051 to the end of SEQ ID NO:3, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Polynucleotides which hybridize to these nucleic acid molecules under stringent hybridization conditions or lower stringency conditions are also encompassed by the invention, as are polypeptides encoded by these polynucleotides.

Also, representative examples of polynucleotide fragments of the invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, or 1401 to the end of SEQ ID NO:5, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Polynucleotides which hybridize to these nucleic acid molecules under stringent hybridization conditions or lower stringency conditions are also encompassed by the invention, as are polypeptides encoded by these polynucleotides.

In the present invention, a "polypeptide fragment" refers to an amino acid sequence which is a portion of that contained in SEQ ID NO:2 or encoded by the cDNA contained in a deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1–20, 2140, 41–60, 61–80, 81–100, 102–120, 121–140, 141–160, 161–180, 181–200, 201–220, 221–240, 241–260, 261–280, 281–300, 301–320, 321–340, 341–360, 361–380, 381400, 401–420, or 421 to the end of the coding region of SEQ ID NO:2. Moreover, polypeptide fragments can be at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, or 430 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

In the present invention, a "polypeptide fragment" also refers to an amino acid sequence which is a portion of that contained in SEQ ID NO:4 or encoded by the cDNA contained in a deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1–20, 21–40, 41–60, 61–80, 81–100, 102–120, 121–140, 141–160, 161–180, 181–200, 201–220, 221–240, 241–260, 261–280, 281–300, 301–320, 321–340, or 341 to the end of the coding region of SEQ ID NO:4. Moreover, polypeptide fragments can be at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, or 350 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

In the present invention, a "polypeptide fragment" also refers to an amino acid sequence which is a portion of that contained in SEQ ID NO:6 or encoded by the cDNA contained in a deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1–20, 21–40, 41–60, 61–80, 81–100, 102–120, 121–140, 141–160, 161–180, 181–200, 201–220, or 221 to the end of the coding region of SEQ ID NO:6. Moreover, polypeptide fragments can be at least about 20, 30, 40, 50, 60, 70, 80, 90, 100, 110, 120, 130, 140, 150, 160, 170, 180, 190, 200, 210, or 220 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

The polynucleotide fragments, specified in contiguous nucleotides, can be immediately envisaged using the above description and are therefore not individually listed solely for the purpose of not unnecessarily lengthening the specification.

The present invention also provides for the exclusion of any fragment, specified by 5' and 3' base positions or by size in nucleotide bases as described above for any nucleotide sequence of the sequence listing or deposited clones. Any number of fragments of nucleotide sequences specified by 5' and 3' base positions or by size in nucleotides, as described above, may be excluded from the present invention.

In the present invention, a "polypeptide fragment" refers to a short amino acid sequence contained in SEQ ID NO:Y or encoded by the cDNA contained in the deposited clone. Protein fragments may be "free-standing," or comprised within a larger polypeptide of which the fragment forms a part or region, most preferably as a single continuous region.

Fragments include portions of the amino acid sequences of the sequence listing and encoded by deposited cDNA clones, at least 7 contiguous amino acid in length, selected from any two integers, one of which representing a N-terminal position and another representing a C-terminal position. The first, or N-terminal most, codon of each polypeptide disclosed herein is position 1. Every combination of a N-terminal and C-terminal position that a fragment at least 7 contiguous amino acid residues in length could occupy, on any given amino acid sequence is included in the invention as an individual specie. At least means a fragment may be 7 contiguous amino acid residues in length or any integer between 7 and the number of residues in a full length amino acid sequence minus 1. Therefore, included in the invention are species of contiguous fragments specified by any N-terminal and C-terminal positions of amino acid sequence set forth in the sequence listing or encoded by the deposited cDNA clones, wherein the contiguous fragment is any integer between 7 and the number of residues in a full length sequence minus 1. The polypeptide fragments specified by N-terminal and C-terminal positions can be immediately envisaged using the above description and are therefore not individually listed solely for the purpose of not unnecessarily lengthening the specification. Althouth it is particularly pointed out that each of the above described species are included in the present invention.

Particularly, N-terminal deletions of the CMP Sialic Acid Synthetase polypeptide can be described by the general formula $m^1$-434, where $m^1$ is an integer from 2 to 428, where $m^1$ corresponds to the position of the amino acid residue identified in SEQ ID NO:2. More in particular, the invention provides polynucleotides encoding polypeptides comprising, or alternatively consisting of, a sequence selected from: D-2 to K434; S-3 to K-434; V4 to K-434; E-5 to K-434; K-6 to K-434; G-7 to K-434; A-8 to K-434; A-9 to K-434; T-10 to K-434; S-11 to K-434; V-12 to K-434; S-13 to K-434; N-14 to K-434; P-15 to K-434; R-16 to K-434; G-17 to K-434; R-18 to K-434; P-19 to K-434; S-20 to K-434; R-21 to K-434; G-22 to K-434; R-23 to K-434; P-24 to K-434;P-25 to K-434; K-26 to K-434; L-27 to K-434; Q-28 to K-434; R-29 to K-434; N-30 to K-434; S-31 to K-434; R-32 to K-434; G-33 to K-434; G-34 to K-434; Q-35 to K-434; G-36 to K-434; R-37 to K-434;G-38 to K-434; V-39 to K-434; E-40 to K-434; K-41 to K-434; P-42 to K-434; P-43 to K-434; H-44 to K-434; L-45 to K-434; A-46 to K-434; A-47 to K-434; L-48 to K-434; I-49 to K-434; L-50 to K-434;A-51 to K-434; R-52 to K-434; G-53 to K-434; G-54 to K-434; S-55 to K-434; K-56 to K-434; G-57 to K-434; I-58 to K-434; P-59 to K-434; L-60 to K-434; K-61 to K-434; N-62 to K-434; 1-63 to K-434;K-64 to K-434; H-65 to K-434; L-66 to K-434; A-67 to K-434; G-68 to K-434; V-69 to K-434; P-70 to K-434; L-71 to K-434; 1-72 to K-434; G-73 to K-434; W-74 to K-434; V-75 to K-434; L-76 to K-434;R-77 to K-434; A-78 to K-434; A-79 to K-434; L-80 to K-434; D-81 to K-434; S-82 to K-434; G-83 to K-434; A-84 to K-434; F-85 to K-434; Q-86 to K-434; S-87 to K-434; V-88 to K-434; W-89 to K-434;V-90 to K-434; S-91 to K-434; T-92 to K-434; D-93 to K-434; H-94 to K-434; D-95 to K-434; E-96 to K-434; I-97 to K-434; E-98 to K-434; N-99 to K-434; V-100 to K-434; A-101 to K-434; K-102 to K-434; Q-103 to K-434; F-104 to K-434; G-105 to K-434; A-106 to K-434; Q-107 to K-434; V-108 to K-434; H-109 to K-434; R-110 to K-434; R-111 to K-434; S-112 to K-434; S-113 to K-434; E-114 to K-434; V-115 to K-434; S-116 to K-434; K-117 to K-434; D-118 to K-434; S-119 to K-434; S-120 to K-434; T-121 to K-434; S-122 to K-434; L-123 to K-434; D-124 to K-434; A-125 to K-434; K-126 to K-434; I-127 to K434; E-128 to K-434; F-129 to K434; L-130 to K-434; N-131 to K-434; Y-132 to K-434; X-133 to K-434; N-134 to K-434; E-135 to K-434; X-136 to K-434; D-137 to K-434; I-138 to K-434; V-139 to K-434; G-140 to K-434; N-141 to K-434;-142 to K-434; Q-143 to K-434; A-144 to K-434; T-145 to K-434; S-146 to K-434; X-147 to K-434; C-148 to K-434; L-149 to K-434; H-150 to K-434; P-151 to K-434; T-152 to K-434; D-153 to K-434; L-154 to K-434; Q-155 to K-434; K-156 to K-434; V-157 to K-434; A-158 to K-434; E-59 to K-434; M-160 to K-434; I-161 to K-434; R-162 to K-434; E-163 to K-434; E-164 to K-434; G-165 to K-434; Y-166 to K-434; D-167 to K-434; S-168 to K-434; X-169 to K-434; F-170 to K-434; S-171 to K-434; V-172 to K-434; V-173 to K-434; R-174 to K-434; R-175 to K-434; H-176 to K-434; Q-177 to K-434; F-178 to K-434; R-179 to K-434; W-180 to K-434; S-181 to K-434; E-182 to K-434; I-183 to K-434; Q-184 to K-434; K-185 to K-434; G-186 to K-434; V-187 to K-434; R-188 to K-434; E-189 to K-434; V-190 to K-434; T-191 to K-434; E-192 to K-434; P-193 to K-434; L-194 to K-434; N-195 to K-434; L-196 to K-434; N-197 to K-434; P-198 to K-434; A-199 to K-434; K-200 to K-434; R-201 to K-434; P-202 to K-434; R-203 to K-434; R-204 to K-434; Q-205 to K-434; D-206 to K-434; W-207 to K-434; D-208 to K-434; G-209 to K-434; E-210 to K-434; L-21 to K-434; Y-212 to K-434; E-213 to K-434; N-214 to K-434; G-215 to K-434; S-216 to K-434; F-217 to K-434; Y-218 to K-434; F-219 to K-434; A-220 to K-434; K-221 to K-434; K-222 to K-434; H-223 to K-434; L-224 to K-434; I-225 to K-434; E-226 to K-434; M-227 to K-434; G-228 to K-434; Y-229 to K-434; L-230 to K-434; Q-231 to K-434; G-232 to K-434; G-233 to K-434; K-234 to K-434; W-235 to K-434; H-236 to K-434; T-237 to K-434; T-238 to K-434; K-239 to K-434; C-240 to K-434; E-241 to K-434; L-242 to K-434; E-243 to K-434; H-244 to K-434; S-245 to K-434; V-246 to K-434; D-247 to K-434; I-248 to K-434; D-249 to K-434; V-250 to K-434; D-251 to K-434; I-252 to K-434; D-253 to K-434; W-254 to K-434; P-255 to K-434; I-256 to K-434; A-257 to K-434; E-258 to K-434; Q-259 to K-434; R-260 to K-434; V-261 to K-434; L-262 to K-434; R-263 to K-434; Y-264 to K-434; G-265 to K-434; Y-266 to K-434; F-267 to K-434; G-268 to K-434; K-269 to K-434; E-270 to K-434; K-271 to K-434; L-272 to K-434; K-273 to K-434; E-274 to K-434; I-275 to K-434; K-276 to K-434; L-277 to K-434; L-278 to K-434; V-279 to K-434; C-280 to K-434; N-281 to K-434; 1-282 to K-434; D-283 to K-434; G-284 to K-434; C-285 to K-434; L-286 to K-434; T-287 to K-434; N-288 to K-434; G-289 to K-434; H-290 to K-434; 1-291 to K-434; Y-292 to K-434; V-293 to K-434; S-294 to K-434; G-295 to K-434; D-296 to K-434; Q-297 to K-434; K-298 to K-434; E-299 to K-434; i-300 to K-434; 1-301 to K-434; S-302 to K434; Y-303 to K-434; D-304 to K-434; V-305 to K-434; K-306 to K-434; D-307 to K-434; A-308 to K-434; I-309 to K-434; Q-310 to K-434; I-311 to K-434; S-312 to K-434; L-313 to K-434; L-314 to K-434; K-315 to K-434; K-316 to K-434; S-317 to K-434; G-318 to K-434; I-319 to K-434; E-320 to K-434; V-321 to K-434; R-322 to K-434; L-323 to K-434; I-324 to K-434; S-325 to K-434; E-326 to K-434; R-327 to K-434; A-328 to K-434; C-329 to K-434; S-330 to K-434; K-331 to K-434; Q-332 to K-434; T-333 to K-434; L-334 to K-434; S-335 to K-434; S-336 to K-434; L-337 to K-434; K-338 to K-434; L-339 to K-434; D-340 to K-434; C-341 to K-434; K-342 to K-434; M-343 to K-434; E-344 to K-434; V-345 to K-434; S-346 to K-434; V-347 to K-434; S-348 to K-434; D-349 to K-434; K-350 to K-434; L-351 to K-434; A-352 to K-434; V-353 to K-434; V-354 to K-434; D-355 to K-434; E-356 to K-434; W-357 to K-434; R-358 to K-434; K-359 to K-434; E-360 to K-434; M-361 to K-434; G-362 to K-434; L-363 to K-434; C-364 to K-434; W-365 to K-434; K-366 to K-434; E-367 to K-434; V-368 to K-434; A-369 to K-434; Y-370 to K-434; L-371 to K-434; G-372 to K-434; N-373 to K-434; E-374 to K-434; V-375 to K-434; S-376 to K-434; D-377 to K-434; E-378 to K-434; E-379 to K-434; C-380 to K-434; L-381 to K-434; K-382 to K-434; R-383 to K-434; V-384 to K-434; G-385 to K-434; L-386 to K-434; S-387 to K-434; G-388 to K-434; A-389 to K-434; P-390 to K-434; A-391 to K-434; D-392 to K-434; A-393 to K-434; C-394 to K-434; S-395 to K-434; Y-396 to K-434; A-397 to K-434; Q-398 to K-434; K-399 to K-434; A-400 to K-434; V-401 to K-434; G-402 to K-434; Y-403 to K-434; I-404 to K-434; C-405 to K-434; K-406 to K-434; C-407 to K-434; N-408 to K-434; G-409 to K-434; G-410 to K-434; R-411 to K-434; G412 to K-434; A-413 to K-434; 1-414 to K-434; R-415 to K-434; E-416 to K-434; F-417 to K-434; A-418 to K-434; E-419 to K-434; H-420 to K-434; I-421 to K-434; C-422 to K-434; L-423 to K-434; L-424 to K-434; M-425 to K-434; E-426 to K434; K-427 to K-434; V-428 to K-434; and N-429 to K-434 of SEQ ID NO:2. Polypeptides encoded by the polynucleotides are also encompassed by the invention.

N-terminal deletions of the Sialic Acid Synthetase polypeptide can be described by the general formula $m^2$-359, where $m^2$ is an integer from 2 to 353, where $m^2$ corresponds to the position of the amino acid residue identified in SEQ ID NO:4. More in particular, the invention provides polynucleotides encoding polypeptides comprising, or alternatively consisting of, a sequence selected from: P-2 to S-359; L-3 to S-359; E-4 to S-359;L-5 to S-359; E-6 to S-359; L-7 to S-359; C-8 to S-359; P-9 to S-359; G-10 to S-359; R-11 to S-359; W-12 to S-359; V-13 to S-359; G-14 to S-359; G-15 to S-359; Q-16 to S-359; H-17 to S-359; P-18 to S-359; C-19 to S-359; F-20 to S-359; 1-21 to S-359; I-22 to S-359; A-23 to S-359; E-24 to S-359; I-25 to S-359;G-26 to S-359; Q-27 to S-359; N-28 to S-359; H-29 to S-359;Q-30 to S-359; G-31 to S-359; D-32 to S-359; L-33 to S-359;D-34 to S-359; V-35 to S-359; A-36 to S-359; K-37 to S-359;R-38 to S-359; M-39 to S-359; I-40 to S-359; R-41 to S-359;M-42 to S-359; A-43 to S-359; K-44 to S-359; E-45 to S-359;C-46 to S-359; G-47 to S-359; A-48 to S-359; D49 to S-359;C-50 to S-359; A-51 to S-359; K-52 to S-359; F-53 to S-359;Q-54 to S-359; K-55 to S-359; S-56 to S-359; E-57 to S-359; L-58 to S-359; E-59 to S-359; F-60 to S-359; K-61 to S-359; F-62 to S-359; N-63 to S-359; R-64 to S-359; K-65 to S-359; A-66 to S-359; L-67 to S-359; E-68 to S-359; R-69 to S-359; P-70 to S-359; Y-71 to S-359; T-72 to S-359; S-73 to S-359; K-74 to S-359; H-75 to S-359; S-76 to S-359; W-77 to S-359; G-78 to S-359; K-79 to S-359; T-80 to S-359;-Y-81 to S-359; G-82 to S-359; E-83 to S-359; H-84 to S-359; K-85 to S-359; R-86 to S-359; H-87 to S-359; L-88 to S-359; E-89 to S-359; F-90 to S-359; S-91 to S-359; H-92 to S-359; D-93 to S-359; Q-94 to S-359; Y-95 to S-359; R-96 to S-359; E-97 to S-359; L-98 to S-359; Q-99 to S-359; R-100 to S-359; Y-101 to S-359; A-102 to S-359; E-103 to S-359; E-104 to S-359; V-105 to S-359; G-106 to S-359; 1-107 to S-359; F-108 to S-359; F-109 to S-359; T-110 to S-359; A-111 to S-359; S-112 to S-359; G-113 to S-359; M-114 to S-359; D-115 to S-359; E-116 to S-359; M-117 to S-359; A-118 to S-359; V-119 to S-359; E-120 to S-359; F-121 to S-359; L-122 to S-359; H-123 to S-359; E-124 to S-359; L-125 to S-359; N-126 to S-359; V-127 to S-359; P-128 to S-359; F-129 to S-359; F-130 to S-359; K-131 to S-359; V-132 to S-359; G-133 to S-359; S-134 to S-359; G-135 to S7359; D-136 to S-359; T-137 to S-359; N-138 to S-359; N-139 to S-359; F-140 to S-359; P-141 to S-359; Y-142 to S-359; L-143 to S-359; E-144 to S-359; K-145 to S-359; T-146 to S-359; A-147 to S-359; K-148 to S-359; K-149 to S-359; G-150 to S-359; R-151 to S-359; P-152 to S-359; M-153 to S-359; V-154 to S-359; I-155 to S-359; S-156 to S-359; S-157 to S-359; G-158 to S-359; M-159 to S-359; Q-160 to S-359; S-161 to S-359;M-162 to S-359; D-163 to S-359; T-164 to S-359; M-165 to S-359; K-166 to S-359; Q-167 to S-359; V-168 to S-359; Y-169 to S-359; Q-170 to S-359; I-171 to S-359; V-172 to S-359; K-173 to S-359; P-174 to S-359; L-175 to S-359; N-176 to S-359; P-177 to S-359; N-178 to S-359; F-179 to S-359; C-180 to S-359; F-181 to S-359; L-182 to S-359; Q-183 to S-359; C-184 to S-359; T-185 to S-359; S-186 to S-359; A-187 to S-359; Y-188 to S-359; P-189 to S-359; L-190 to S-359; Q-191 to S-359; P-192 to S-359; E-193 to S-359; D-194 to S-359; V-195 to S-359; N-196 to S-359; L-197 to S-359; R-198 to S-359; V-199 to S-359; I-200 to S-359; S-201 to S-359; E-202 to S-359; Y-203 to S-359; Q-204 to S-359; K-205 to S-359; L-206 to S-359; F-207 to S-359; P-208 to S-359; D-209 to S-359; I-210 to S-359; P-211 to S-359; 1-212 to S-359; G-213 to S-359; Y-214 to S-359; S-215 to S-359; G-216 to S-359; H-217 to S-359; E-218 to S-359; T-219 to S-359; G-220 to S-359; I-221 to S-359; A-222 to S-359; 1-223 to S-359; S-224 to S-359; V-225 to S-359; A-226 to S-359; A-227 to S-359; V-228 to S-359; A-229 to S-359; L-230 to S-359; G-231 to S-359; A-232 to S-359; K-233 to S-359; V-234 to S-359; L-235 to S-359; E-236 to S-359; R-237 to S-359; H-238 to S-359; I-239 to S-359; T-240 to S-359; L-241 to S-359; D-242 to S-359; K-243 to S-359; T-244 to S-359; W-245 to S-359; K-246 to S-359; G-247 to S-359; S-248 to S-359; D-249 to S-359; H-250 to S-359; S-251 to S-359; A-252 to S-359; S-253 to S-359; L-254 to S-359; E-255 to S-359; P-256 to S-359; G-257 to S-359; E-258 to S-359; L-259 to S-359; A-260 to S-359; E-261 to S-359; L-262 to S-359; V-263 to S-359; R-264 to S-359; S-265 to S-359; V-266 to S-359; R-267 to S-359; L-268 to S-359; V-269 to S-359; E-270 to S-359; R-271 to S-359; A-272 to S-359; L-273 to S-359; G-274 to S-359; S-275 to S-359; P-276 to S-359; T-277 to S-359; K-278 to S-359; Q-279 to S-359; L-280 to S-359; L-281 to S-359; P-282 to S-359; C-283 to S-359; E-284 to S-359; M-285 to S-359; A-286 to S-359; C-287 to S-359; N-288 to S-359; E-289 to S-359; K-290 to S-359; L-291 to S-359; G-292 to S-359; K-293 to S-359; S-294 to S-359; V-295 to S-359; V-296 to S-359; A-297 to S-359; K-298 to S-359; V-299 to S-359; K-300 to S-359; I-301 to S-359; P-302 to S-359; E-303 to S-359; G-304 to S-359; T-305 to S-359; 1-306 to S-359; L-307 to S-359; T-308 to S-359; M-309 to S-359; D-310 to S-359; M-311 to S-359; L-312 to S-359; T-313 to S-359; V-314 to S-359; K-315 to S-359; V-316 to S-359; G-317 to S-359; E-318 to S-359; P-319 to S-359; K-320 to S-359; A-321 to S-359; Y-322 to S-359; P-323 to S-359; P-324 to S-359; E-325 to S-359; D-326 to S-359; 1-327 to S-359; F-328 to S-359; N-329 to S-359; L-330 to S-359; V-331 to S-359; G-332 to S-359; K-333 to S-359; K-334 to S-359; V-335 to S-359; L-336 to S-359; V-337 to S-359; T-338 to S-359; V-339 to S-359; E-340 to S-359; E-341 to S-359; D-342 to S-359; D-343 to S-359; T-344 to S-359; I-345 to S-359; M-346 to S-359; E-347 to S-359; E-348 to S-359; L-349 to S-359; V-350 to S-359; D-351 to S-359; N-352 to S-359; H-353 to S-359; and G-354 to S-359 of SEQ ID NO:4. Polypeptides encoded by these polynucleotides are also encompassed by the invention.

N-terminal deletions of the Aldolase polypeptide can be described by the general formula $m^3$-230, where $m^3$ is an integer from 2 to 224, where $m^3$ corresponds to the position of the amino acid residue identified in SEQ ID NO:6. More in particular, the invention provides polynucleotides encoding polypeptides comprising, or alternatively consisting of, a sequence selected from: A-2 to N-230; F-3 to N-230; P4 to N-230; K-5 to N-230; K-6 to N-230; K-7 to N-230; L-8 to N-230; Q-9 to N-230; G-10 to N-230; L-11 to N-230; V-12 to N-230; A-13 to N-230; A-14 to N-230; T-15 to N-230; I-16 to N-230; T-17 to N-230; P-18 to N-230; M-19 to N-230; T-20 to N-230; E-21 to N-230; N-22 to N-230; G-23 to N-230; E-24 to N-230; I-25 to N-230; N-26 to N-230; F-27 to N-230; S-28 to N-230; V-29 to N-230; I-30 to N-230; G-31 to N-230; Q-32 to N-230; Y-33 to N-230; V-34 to N-230; D-35 to N-230; Y-36 to N-230; L-37 to N-230; V-38 to N-230; K-39 to N-230; E-40 to N-230; Q-41 to N-230; G-42 to N-230; V-43 to N-230; K-44 to N-230; N45 to N-230; I-46 to N-230; F-47 to N-230; V-48 to N-230; N-49 to N-230; G-50 to N-230; T-51 to N-230; T-52 to N-230; G-53 to N-230; E-54 to N-230; G-55 to N-230; L-56 to N-230; S-57 to N-230; L-58 to N-230; S-59 to N-230; V-60 to N-230; S-61 to N-230; E-62 to N-230; R-63 to N-230; R-64 to N-230; Q-65 to N-230; V-66 to N-230; A-67 to N-230; E-68 to N-230; E-69 to N-230; W-70 to N-230; V-71 to N-230; T-72 to N-230; K-73 to N-230; G-74 to N-230; K-75 to N-230; D-76 to N-230; K-77 to N-230; L-78 to N-230; D-79 to N-230; Q-80 to N-230; V-81 to N-230; I-82 to N-230; I-83 to N-230; H-84 to N-230; V-85 to N-230; G-86 to N-230; A-87 to N-230; L-88 to N-230; S-89 to N-230; L-90 to N-230; K-91 to N-230; E-92 to N-230; S-93 to N-230; Q-94 to N-230; E-95 to N-230; L-96 to N-230; A-97 to N-230; Q-98 to N-230; H-99 to N-230; A-100 to N-230; A-101 to N-230; E-102 to N-230; I-103 to N-230; G-104 to N-230;A-105 to N-230; D-106 to N-230; G-107 to N-230; I-108 to N-230; A-109 to N-230; V-110 to N-230; I-111 to N-230; A-112 to N-230; P-113 to N-230; F-114 to N-230; F-i 15 to N-230; L-116 to N-230; K-117 to N-230;P-118 to N-230; W-119 to N-230; T-120 to N-230; K-121 to N-230; D-122 to N-230; I-123 to N-230; L-124 to N-230; I-125 to N-230; N-126 to N-230; F-127 to N-230; L-128 to N-230; K-129 to N-230; E-130 to N-230;V-131 to N-230; A-132 to N-230; A-133 to N-230; A-134 to N-230; A-135 to N-230; P-136 to N-230; A-137 to N-230; L-138 to N-230; P-139 to N-230; F-140 to N-230; Y-141 to N-230; Y-142 to N-230; Y-143 to N-230;H-144 to N-230; I-145 to N-230; P-146 to N-230; A-147 to N-230; L-148 to N-230; T-149 to N-230; G-150 to N-230; V-151 to N-230; K-152 to N-230; I-153 to N-230; R-154 to N-230; A-155 to N-230; E-156 to N-230;E-157 to N-230; L-158 to N-230; L-159 to N-230; D-160 to N-230; G-161 to N-230; I-162 to N-230; L-163 to N-230; D-164 to N-230; K-165 to N-230; I-166 to N-230; P-167 to N-230; T-168 to N-230; F-169 to N-230;Q-170 to N-230; G-171 to N-230; L-172 to N-230; K-173 to N-230; F-174 to N-230; S-175 to N-230; D-176 to N-230; T-177 to N-230; D-178 to N-230; L-179 to N-230; L-180 to N-230; D-181 to N-230; F-182 to N-230;G-183 to N-230; Q-184 to N-230; C-185 to N-230; V-186 to N-230; D-1-87 to N-230; Q-188 to N-230; N-189 to N-230; R-190 to N-230; Q-191 to N-230; Q-192 to N-230; Q-193 to N-230; F-194 to N-230; A-195 to N-230;F-196 to N-230; L-197 to N-230; F-198 to N-230; G-199 to N-230; V-200 to N-230; D-201 to N-230; E-202 to N-230; Q-203 to N-230; L-204 to N-230; L-205 to N-230; S-206 to N-230; A-207 to N-230; L-208 to N-230;V-209 to N-230; M-210 to N-230; G-211 to N-230; A-212 to N-230; T-213 to N-230; G-214 to N-230; A-215 to N-230; V-216 to N-230; G-217 to N-230; S-218 to N-230; F-219 to N-230; V-220 to N-230; S-221 to N-230;R-222 to N-230; D-223 to N-230; L-224 to N-230; and S-225 to N-230 of SEQ ID NO:6. Polypeptides encoded by these polynucleotides are also encompassed by the invention.

Further, the invention includes polypeptides comprising sub-genuses of fragments specified by size, in amino acid residues, rather than by N-terminal and C-terminal positions. The invention includes any fragment size, in contiguous amino acid residues, selected from integers between 7 and the number of residues in a full length sequence minus 1. Preferred sizes of contiguous polypeptide fragments include at least 7 amino acid residues, at least 10 amino acid residues, at least 20 amino acid residues, at least 30 amino acid residues, at least 40 amino acid residues, at least 50 amino acid residues, at least 75 amino acid residues, at least 100 amino acid residues, at least 125 amino acid residues, at least 150 amino acid residues, at least 175 amino acid residues, at least 200 amino acid residues, at least 225 amino acid residues, at least 250 amino acid residues, at least 275 amino acid residues, at least 300 amino acid residues, at least 325 amino acid residues, at least 350 amino acid residues, at least 375 amino acid residues, at least 400 amino acid residues, at least 425 amino acid residues, and at least 450 amino acid residues. The preferred sizes are, of course, meant to exemplify, not limit, the present invention as all size fragments representing any integer between 7 and the number of residues in a full length sequence minus 1 are included in the invention.

The contiguous polypeptide fragments specified by size in amino acid residues of the present invention can be immediately envisaged using the above description and are therefore not individually listed solely for the purpose of not unnecessarily lengthening the specification.

The present-invention also provides for the exclusion of any fragments specified by N-terminal and C-terminal positions or by size in amino acid residues as described above. Any number of fragments specified by N-terminal and C-terminal positions or by size in amino acid residues as described above.

It is particularly pointed out that the above fragments need not be active since they would be useful, for example, in immunoassays, in epitope mapping, epitope tagging, to generate antibodies to a particular portion of the polypeptide, as vaccines, and as molecular weight markers.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotide fragments encoding these domains are also contemplated.

Other preferred fragments are biologically active fragments. Biological activity of fragments of the polypeptides of the invention can be determined using or routinely modifying assays known in the art. Biologically active fragments are those exhibiting activity similar, but not necessarily identical, to an activity of the polypeptide of the present invention. The biological activity of the fragments may include an improved desired activity, or a decreased undesirable activity.

In another aspect, the invention provides peptides and polypeptides comprising epitope-bearing portions of CMP Sialic Acid Synthetase, Sialic Acid Synthetase, and/or Aldolase polypeptides of the present invention. These epitopes are immunogenic or antigenic epitopes of the polypeptides of the present invention. An "immunogenic epitope" is defined as a part of a protein that elicits an antibody response in vivo when the whole polypeptide of the present invention, or fragment thereof, is the immunogen. On the other hand, a region of a polypeptide to which an antibody can bind is defined as an "antigenic determinant" or "antigenic epitope." The number of in vivo immunogenic epitopes of a protein generally is less than the number of antigenic epitopes. See, e.g., Geysen, et al. (1983) Proc. Natl. Acad. Sci. USA 81:3998–4002. However, antibodies can be made to any antigenic epitope, regardless of whether it is an immunogenic epitope, by using methods such as phage display. See e.g., Petersen G. et al. (1995) Mol. Gen. Genet. 249:425–431. Therefore, included in the present invention are both immunogenic epitopes and antigenic epitopes.

A list of exemplified amino acid sequences comprising immunogenic epitopes of the invention are described elsewhere herein. It is pointed out that these descriptions only listamino acid residues comprising epitopes predicted to have the highest degree of antigenicity using the algorithm of Jameson and Wolf, (1988) Comp. Appl. Biosci. 4:181–186 (said references incorporated by reference in their entireties). The Jameson-Wolf antigenic analysis was performed using the computer program PROTEAN, using default parameters (Version 3.11 for the Power MacIntosh, DNASTAR, Inc., 1228 South Park Street Madison, Wis.). Amino acid residues comprising other immunogenic epitopes may be routinely determined using algorithms similar to the Jameson-Wolf analysis or by in vivo testing for an antigenic response using methods known in the art. See, e.g., Geysen et al., supra; U.S. Pat. Nos. 4,708,781; 5,194,392; 4,433,092; and 5,480,971 (said references incorporated by reference in their entireties).

It is particularly pointed out that the described epitopic amino acid sequences comprise immunogenic epitopes. Thus, additional flanking residues on either the N-terminal, C-terminal, or both N- and C-terminal ends may be added to the sequences to generate an epitope-bearing polypeptide of the present invention. Therefore, the immunogenic epitopes may include additional N-terminal or C-terminal amino acid residues. The additional flanking amino acid residues may be contiguous flanking N-terminal and/or C-terminal sequences from the polypeptides of the present invention, heterologous polypeptide sequences, or may include both contiguous flanking sequences from the polypeptides of the present invention and heterologous polypeptide sequences.

Polypeptides of the present invention comprising immunogenic or antigenic epitopes are at least 7 amino acids residues in length. "At least" means that a polypeptide of the present invention comprising an immunogenic or antigenic epitope may be 7 amino acid residues in length or any integer between 7 amino acids and the number of amino acid residues of the full length polypeptides of the invention. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. However, it is pointed out that each and every integer between 7 and the number of amino acid residues of the full length polypeptide are included in the present invention.

The immuno and antigenic epitope-bearing fragments may be specified by either the number of contiguous amino acid residues, as described above, or further specified by N-terminal and C-terminal positions of these fragments on the amino acid sequence of SEQ ID NO:2, 4, or 6. Every combination of a N-terminal and C-terminal position that a fragment of, for example, at least 7 or at least 15 contiguous amino acid residues in length could occupy on the amino acid sequence of SEQ ID NO:2, 4, or 6 is included in the invention. Again, "at least 7 contiguous amino acid residues in length" means 7 amino acid residues in length or any integer between 7 amino acids and the number of amino acid residues of the full length polypeptide of the present invention. Specifically, each and every integer between 7 and the number of amino acid residues of the full length polypeptide are included in the present invention.

Immunogenic and antigenic epitope-bearing polypeptides of the invention are useful, for example, to make antibodies which specifically bind the polypeptides of the invention, and in immunoassays to detect the polypeptides of the present invention. The antibodies are useful, for example, in affinity purification of the polypeptides of the present invention. The antibodies may also routinely be used in a variety of qualitative or quantitative immunoassays, specifically for the polypeptides of the present invention using methods known in the art. See, e.g., Harlow et al., Antibodies: A Laboratory Manual, (Cold Spring Harbor Laboratory Press; 2nd Ed. 1988).

The epitope-bearing polypeptides of the present invention may be produced by any conventional means for making polypeptides including synthetic and recombinant methods known in the art. For instance, epitope-bearing peptides may be synthesized using known methods of chemical synthesis. For instance, Houghten has described a simple method for the synthesis of large numbers of peptides, such as 10–20 mgs of 248 individual and distinct 13 residue peptides representing single amino acid variants of a segment of the HA1 polypeptide, all of which were prepared and characterized (by ELISA-type binding studies) in less than four weeks (Houghten, R. A. Proc. Natl. Acad. Sci. USA 82:5131–5135 (1985)). This "Simultaneous Multiple Peptide Synthesis (SMPS)" process is further described in U.S. Pat. No. 4,631,211 to Houghten and coworkers (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously (Houghten et al., Proc. Natl. Acad. Sci. 82:5131–5135 at 5134 (1985)).

Epitope-bearing polypeptides of the present invention are used to induce antibodies according to methods well known in the art including, but not limited to, in vivo immunization, in vitro immunization, and phage display methods. See, e.g., Sutcliffe, et al., supra; Wilson, et al., supra, and Bittle, et al., J. Gen. Virol. 66:2347–2354 (1985). If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as -maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 $\mu$gs of peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins. See, e.g., EPA 0,394,827; Traunecker et al. (1988) Nature 331:84–86. Fusion proteins that have a disulfide-linked dimeric structure due to the IgG portion can also be more efficient in binding and neutralizing other molecules than monomeric polypeptides or fragments thereof alone. See, e.g., Fountoulakis et al., J. Biochem. 270:3958–3964 (1995). Nucleic acids encoding the above epitopes can also be recombined with a gene of interest as an epitope tag to aid in detection and purification of the expressed polypeptide.

Polynucleotide and Polypeptide Variants

The present invention is directed to variants of the polynucleotide sequences disclosed in SEQ ID NO: 1, SEQ ID NO:3, SEQ ID NO:5, the complementary strands thereto, and/or the cDNA sequences contained in a deposited clone.

The present invention also encompasses variants of the polypeptide sequences disclosed in SEQ ID NO:2, SEQ ID NO:4, SEQ ID NO:6, and/or encoded by a deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

The present invention is also directed to nucleic acid molecules which comprise, or alternatively consist of, a nucleotide sequence which is at least 80%, 85%, 90%, 95%, 96%, 97%, 98% or 99% identical to, for example, the nucleotide coding sequence in SEQ ID NO: 1 or the complementary strand thereto, the nucleotide coding sequence contained in a deposited cDNA clone or the complementary strand thereto, a nucleotide sequence encoding the polypeptide of SEQ ID NO:2, a nucleotide sequence encoding the polypeptide encoded by the cDNA contained in a deposited clone, and/or polynucleotide fragments of any of these nucleic acid molecules (e.g., those fragments described herein). Polynucleotides which hybridize to these nucleic acid molecules under stringent hybridization conditions, or alternatively, under lower stringency conditions are also encompassed by the invention, as are polypeptides encoded by these polynucleotides.

The present invention is also directed to polypeptides which comprise, or alternatively consist of, an amino acid sequence which is at least 80%, 85%, 90%, 95%, 96%, 97%, 98%, 99% identical to, for example, the polypeptide sequence shown in SEQ ID NO:2, the polypeptide sequence encoded by the cDNA contained in a deposited clone, and/or polypeptide fragments of any of these polypeptides (e.g., those fragments described herein).

The present invention is also directed to nucleic acid molecules which comprise, or alternatively consist of, a nucleotide sequence which is at least 80%, 85%, 90%, 95%, 96%, 97%, 98% or 99% identical to, for example, the nucleotide coding sequence in SEQ ID NO:3 or the complementary strand thereto, the nucleotide coding sequence contained in a deposited cDNA clone or the complementary strand thereto, a nucleotide sequence encoding the polypeptide of SEQ ID NO:4, a nucleotide sequence encoding the polypeptide encoded by the cDNA contained in a deposited clone, and/or polynucleotide fragments of any of these nucleic acid molecules (e.g., those fragments described herein). Polynucleotides which hybridize to these nucleic acid molecules under stringent hybridization conditions, or alternatively, under lower stringency conditions are also encompassed by the invention, as are polypeptides encoded by these polynucleotides.

The present invention is also directed to polypeptides which comprise, or alternatively consist of, an amino acid sequence which is at least 80%, 85%, 90%, 95%, 96%, 97%, 98%, 99% identical to, for example, the polypeptide sequence shown in SEQ ID NO:4, the polypeptide sequence encoded by the cDNA contained in a deposited clone, and/or polypeptide fragments of any of these polypeptides (e.g., those fragments described herein).

The present invention is also directed to nucleic acid molecules which comprise, or alternatively consist of, a nucleotide sequence which is at least 80%, 85%, 90%, 95%, 96%, 97%, 98% or 99% identical to, for example, the nucleotide coding sequence in SEQ ID NO:5 or the complementary strand thereto, the nucleotide coding sequence contained in a deposited cDNA clone or the complementary strand thereto, a nucleotide sequence encoding the polypeptide of SEQ ID NO:6, a nucleotide sequence encoding the polypeptide encoded by the cDNA contained in a deposited clone, and/or polynucleotide fragments of any of these nucleic acid molecules (e.g., those fragments described herein). Polynucleotides which hybridize to these nucleic acid molecules under stringent hybridization conditions, or alternatively, under lower stringency conditions are also encompassed by the invention, as are polypeptides encoded by these polynucleotides.

The present invention is also directed to polypeptides which comprise, or alternatively consist of, an amino acid sequence which is at least 80%, 85%, 90%, 95%, 96%, 97%, 98%, 99% identical to, for example, the polypeptide sequence shown in SEQ ID NO:6, the polypeptide sequence encoded by the cDNA contained in a deposited clone, and/or polypeptide fragments of any of these polypeptides (e.g., those fragments described herein).

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in SEQ ID NO:1, SEQ ID NO:3, SEQ ID NO:5, the corresponding ORFs (open reading frames), or any fragments as described herein.

As a practical matter, whether any particular nucleic acid molecule or polypeptide is at least 80%, 85%, 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the lenght of the subject nucleotide sequence, whichever is shorter.

If the subject sequence is shorter than the query sequence because of 5' or 3' deletions, not because of internal deletions, a manual correction must be made to the results. This is becuase the FASTDB program does not account for 5' and 3' truncations of the subject sequence when calculating percent identity. For subject sequences truncated at the 5' or 3' ends, relative to the the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignement of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequnce are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequences shown in the sequence listing or to the amino acid sequence encoded by a deposited cDNA plasmid, or a fragment thereof (e.g., as described herein) can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty= 0.05, Window Size=500 or the length of the subject amino acid sequence, whichever is shorter.

If the subject sequence is shorter than the query sequence due to N- or C-terminal deletions, not because of internal deletions, a manual correction must be made to the results. This is becuase the FASTDB program does not account for N- and C-terminal truncations of the subject sequence when calculating global percent identity. For subject sequences truncated at the N- and C-termini, relative to the the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequnce are manually corrected for. No other manual corrections are to made for the purposes of the present invention.

CMP Sialic Acid Synthetase, Sialic Acid Synthetase, and/or Aldolase variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as E. coli).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1 alpha mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes CMP Sialic Acid Synthetase, Sialic Acid Synthetase, and Aldolase polypeptide variants which show functional activity (e.g., biological activity). Such variants include deletions, insertions, inversions, repeats, and substitutions selected according to general rules known in the art so as have little effect on activity.

The present application is directed to CMP Sialic Acid Synthetase nucleic acid molecules at least 80%, 85%, 90%, 95%, 96%, 97%, 98% or 99% identical to the nucleic acid sequences disclosed herein, (e.g., encoding a polypeptide having the amino acid sequence of an N and/or C terminal deletion disclosed herein as $m^1$–$n^1$ of SEQ ID NO:2), irrespective of whether they encode a polypeptide having CMP Sialic Acid Synthetase functional activity. This is because even where a particular nucleic acid molecule does not encode a polypeptide having CMP Sialic Acid Synthetase functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having CMP Sialic Acid Synthetase functional activity include, inter alia, (1) isolating a CMP Sialic Acid Synthetase gene or allelic or splice variants thereof in a cDNA library; (2) in situ hybridization (e.g., "FISH") to metaphase chromosomal spreads to provide precise chromosomal location of the CMP Sialic Acid Synthetase gene, as described in Verma et al., Human Chromosomes: A Manual of Basic Techniques, Pergamon Press, New York (1988); and (3) Northern Blot analysis for detecting CMP Sialic Acid Synthetase mRNA expression in specific tissues.

Preferred, however, are nucleic acid molecules having sequences at least 80%, 85%, 90%, 95%, 96%, 97%, 98% or 99% identical to the nucleic acid sequences disclosed herein, which do, in fact, encode a polypeptide having CMP Sialic Acid Synthetase functional activity. By "a polypeptide having CMP Sialic Acid Synthetase functional activity" is intended polypeptides exhibiting activity similar, but not necessarily identical, to a functional activity of the CMP Sialic Acid Synthetase polypeptides of the present invention (e.g., complete (full-length) CMP Sialic Acid Synthetase, mature (post-translationally modified) CMP Sialic Acid Synthetase and soluble CMP Sialic Acid Synthetase in a particular immunoassay or biological assay as disclosed herein or otherwise known in the art.

Of course, due to the degeneracy of the genetic code, one of ordinary skill in the art will immediately recognize that a large number of the nucleic acid molecules having a sequence at least 80%, 85%, 90%, 95%, 96%, 97%, 98%, or 99% identical to the nucleic acid sequence of a deposited cDNA, the nucleic acid sequence shown in SEQ ID NO: 1, or fragments thereof, will encode polypeptides "having CMP Sialic Acid Synthetase functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having CMP Sialic Acid Synthetase functional activity. This is because the skilled artisan is fully aware of amino acid substitutions that are either less likely or not likely to significantly effect protein function (e.g., replacing one aliphatic amino acid with a second aliphatic amino acid), as further described below.

The present application is also directed to Sialic Acid Synthetase nucleic acid molecules at least 80%, 85%, 90%, 95%, 96%, 97%, 98% or 99% identical to the nucleic acid sequences disclosed herein, (e.g., encoding a polypeptide having the amino acid sequence of an N and/or C terminal deletion disclosed herein as $m^2$–$n^2$ of SEQ ID NO:4), irrespective of whether they encode a polypeptide having Sialic Acid Synthetase functional activity. This is because even where a particular nucleic acid molecule does not encode a polypeptide having Sialic Acid Synthetase functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having Sialic Acid Synthetase functional activity include, inter alia, (1) isolating a Sialic Acid Synthetase gene or allelic or splice variants thereof in a cDNA library; (2) in situ hybridization (e.g., "FISH") to metaphase chromosomal spreads to provide precise chromosomal location of the Sialic Acid Synthetase gene, as described in Verma et al., Human Chromosomes: A Manual of Basic Techniques, Pergamon Press, New York (1988); and (3) Northern Blot analysis for detecting Sialic Acid Synthetase mRNA expression in specific tissues.

Preferred, however, are nucleic acid molecules having sequences at least 80%, 85%, 90%, 95%, 96%, 97%, 98% or 99% identical to the nucleic acid sequences disclosed herein, which do, in fact, encode a polypeptide having Sialic Acid Synthetase functional activity. By "a polypeptide having Sialic Acid Synthetase functional activity" is intended polypeptides exhibiting activity similar, but not necessarily identical, to a functional activity of the Sialic Acid Synthetase polypeptides of the present invention (e.g., complete (full-length) Sialic Acid Synthetase, mature (post-translationally modified) Sialic Acid Synthetase and soluble CMP Sialic Acid Synthetase in a particular immunoassay or biological assay as disclosed herein or otherwise known in the art.

Of course, due to-the degeneracy of the genetic code, one of ordinary skill in the art will immediately recognize that a large number of the nucleic acid molecules having a sequence at least 80%, 85%, 90%, 95%, 96%, 97%, 98%, or 99% identical to the nucleic acid sequence of a deposited cDNA, the nucleic acid sequence shown in SEQ ID NO:3, or fragments thereof, will encode polypeptides "having Sialic Acid Synthetase functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having Sialic Acid Synthetase functional activity. This is because the skilled artisan is fully aware of amino acid substitutions that are either less likely or not likely to significantly effect protein function (e.g., replacing one aliphatic amino acid with a second aliphatic amino acid), as further described below.

The present application is also directed to Aldolase nucleic acid molecules at least 80%, 85%, 90%, 95%, 96%, 97%, 98% or 99% identical to the nucleic acid sequences disclosed herein, (e.g., encoding a polypeptide having the amino acid sequence of an N and/or C terminal deletion disclosed herein as $m^3$–$n^3$ of SEQ ID NO:6), irrespective of whether they encode a polypeptide having Aldolase functional activity. This is because even where a particular nucleic acid molecule does not encode a polypeptide having Aldolase functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having Aldolase functional activity include, inter alia, (1) isolating a Aldolase gene or allelic or splice variants thereof in a cDNA library; (2) in situ hybridization (e.g., "FISH") to metaphase chromosomal spreads to provide precise chromosomal location of the Aldolase gene, as described in Verma et al., Human Chromosomes: A Manual of Basic Techniques, Pergamon Press, New York (1988); and (3) Northern Blot analysis for detecting Aldolase mRNA expression in specific tissues.

Preferred, however, are nucleic acid molecules having sequences at least 80%, 85%, 90%, 95%, 96%, 97%, 98% or 99% identical to the nucleic acid sequences disclosed herein, which do, in fact, encode a polypeptide having Aldolase functional activity. By "a polypeptide having Aldolase functional activity" is intended polypeptides exhibiting activity similar, but not necessarily identical, to a functional activity of the Aldolase polypeptides of the present invention (e.g., complete (full-length) Aldolase, mature (post-translationally modified) Aldolase and soluble Aldolase in a particular immunoassay or biological assay as disclosed herein or otherwise known in the art.

Of course, due to the degeneracy of the genetic code, one of ordinary skill in the art will immediately recognize that a large number of the nucleic acid molecules having a sequence at least 80%, 85%, 90%, 95%, 96%, 97%, 98%, or 99% identical to the nucleic acid sequence of a deposited cDNA, the nucleic acid sequence shown in SEQ ID NO:5, or fragments thereof, will encode polypeptides "having Aldolase functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having Aldolase functional activity. This is because the skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie, J. U. et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al.; Crit. Rev. Therapeutic Drug Carrier Systems 10:307–377 (1993).)

Antibodies

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92105793; Tutt, A. et al. (1991) J. Immunol. 147:60–69; U.S. Pat. Nos. 5,573,920, 4,474,893, 5,601,819, 4,714,681,4,925,648; Kostelny, S. A. et al. (1992) J. Immunol. 148:1547–1553.

Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., *ANTIBODIES: A LABORATORY MANUAL*, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. Monoclonal antibodies can be prepared using a wide of techniques known in the art including the use of hybridoma and recombinant technology. See, e.g., Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563–681 (Elsevier, N.Y., 1981) (said references incorporated by reference in their entireties). Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995) J. Immunol. Methods 182:41–50; Ames, R. S. et al. (1995) J. Immunol. Methods 184:177–186; Kettleborough, C. A. et al. (1994) Eur. J. Immunol. 24:952–958; Persic, L. et al. (1997) Gene 187 9–18; Burton, D. R. et al. (1994) Advances in Immunology 57:191–280; PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax, R. L. et al. (1992) BioTechniques 12(6):864–869; and Sawai, H. et al. (1995) AJRI 34:26–34; and Better, M. et al. (1988) Science 240:1041–1043 (said references incorporated by reference in their entireties).

Examples of techniques which can be used to produce single-chain Fvs and antibodies include those described in U.S. Pat. No. 4,946,778 and 5,258,498; Huston et al. (1991) Methods in Enzymology 203:46–88; Shu, L. et al. (1993) PNAS 90:7995–7999; and Skerra, A. et al. (1988) Science 240:1038–1040. For some uses, including in vivo use of antibodies in humans and in vitro detection assays, it may be preferable to use chimeric, humanized, or human antibodies. Methods for producing chimeric antibodies are known in the art. See e.g., Morrison, Science 229:1202 (1985); Oi et al., BioTechniques 4:214 (1986); Gillies, S. D. et al. (1989) J. Immunol. Methods 125:191–202; and U.S. Pat. No. 5,807, 715. Antibodies can be humanized using a variety of techniques including CDR-grafting (EP 0 239 400; WO 91/09967; U.S. Pat. No. 5,530,101; and 5,585,089), veneering or resurfacing (EP 0 592 106; EP 0 519 596; Padlan E. A., (1991) Molecular Immunology 28(4/5):489–498; Studnicka G. M. et al. (1994) Protein Engineering 7(6):805–814; Roguska M. A. et al. (1994) PNAS 91:969–973), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; and WO 98/46645 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al. (1994) Immunol. Lett. 39:91–99; U.S. Pat. No. 5,474, 981; Gillies, S. O. et al. (1992) PNAS 89:1428–1432; Fell, H. P. et al. (1991) J. Immunol. 146:2446–2452 (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991) PNAS 88:10535–10539; Zheng, X. X. et al. (1995) J. Immunol. 154:5590–5600; and Vil, H. et al. (1992) PNAS 89:11337–11341 (said references incorporated by reference in their entireties).

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al. (1998) Blood 92(6):1981–1988; Chen, Z. et al. (1998) Cancer Res. 58(16): 3668–3678; Harrop, J. A. et al. (1998) J. Immunol. 161(4): 1786–1794; Zhu, Z. et al. (1998) Cancer Res. 58(15): 3209–3214; Yoon, D. Y. et al. (1998) J. Immunol. 160(7): 3170–3179; Prat, M. et al. (1998) J. Cell. Sci. 111(Pt2): 237–247; Pitard, V. et al. (1997) J. Immunol. Methods 205(2):177–190; Liautard, J. et al. (1997) Cytokinde 9(4): 233–241; Carlson, N. G. et al. (1997) J. Biol. Chem. 272(17):11295–11301; Taryman, R. E. et al. (1995) Neuron 14(4):755–762; Muller, Y. A. et al. (1998) Structure 6(9): 1153–1167; Bartunek, P. et al. (1996) Cytokine 8(1):14–20 (said references incorporated by reference in their entireties).

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgG), as described above, resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked. In addition, a methionine codon may be appropriately added to vectors of the present invention, for the proper translation of polypeptides of the present invention which lack an N-terminal methionine.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

In addition to the foregoing, a polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as detection and diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).) Thus, the invention provides a detection or diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a marker for a cell type, cell condition, or disorder.

Moreover, polypeptides of the present invention can be used to treat disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by absorbing free ligand (e.g., soluble TNF receptors used in reducing inflammation), or to bring about a desired response (e.g., blood vessel growth).

Similarly, antibodies directed to a polypeptide of the present invention can also be used to treat disease. For example, administration of an antibody directed to a polypeptide of the present invention can bind and reduce levels of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Immune Activity

A polypeptide or polynucleotide of the present invention may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, a polynucleotide or polypeptide of the present invention can be used as a marker or detector of a particular immune system disease or disorder.

A polynucleotide or polypeptide of the present invention may be useful in treating or detecting deficiencies or disorders of hematopoietic cells. A polypeptide or polynucleotide of the present invention could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polypeptide or polynucleotide of the present invention could also be used to modulate hemostatic (the stopping of bleeding) or thrombolytic activity (clot formation). For example, by increasing hemostatic or thrombolytic activity, a polynucleotide or polypeptide of the present invention could be used to treat blood coagulation disorders (e.g., afibrinogenemia, factor deficiencies), blood platelet disorders (e.g. thrombocytopenia), or wounds resulting from trauma, surgery, or other causes. Alternatively, a polynucleotide or polypeptide of the present invention that can decrease hemostatic or thrombolytic activity could be used to inhibit or dissolve clotting. These molecules could be important in the treatment of heart attacks (infarction), strokes, or scarring.

A polynucleotide or polypeptide of the present invention may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of a polypeptide or polynucleotide of the present invention that inhibits an immune response, particularly the proliferation, differentiation, or chemotaxis of T-cells, may be an effective therapy in preventing autoimmune disorders. For example, soluble forms of the polynucleotides of the present invention may be useful in inhibiting cytokine activity by absorption.

Examples of autoimmune disorders that can be treated or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitus, and autoimmune inflammatory eye disease.

Similarly, allergic reactions and conditions, such as asthma (particularly allergic asthma) or other respiratory problems, may also be treated by a polypeptide or polynucleotide of the present invention. Moreover, these molecules can be used to treat anaphylaxis, hypersensitivity to an antigenic molecule, or blood group incompatibility.

A polynucleotide or polypeptide of the present invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues.

The administration of a polypeptide or polynucleotide of the present invention that inhibits an immune response, particularly the proliferation, differentiation, or chemotaxis of T-cells, may be an effective therapy in preventing organ rejection or GVHD.

Similarly, a polypeptide or polynucleotide of the present invention may also be used to modulate inflammation. For example, the polypeptide or polynucleotide may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polypeptide or polynucleotide can be used to treat or detect hyperproliferative disorders, including neoplasms. A polypeptide or polynucleotide of the present invention may inhibit the proliferation of the disorder through direct or indirect interactions. Alternatively, a polypeptide or polynucleotide of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by a polynucleotide or polypeptide of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by a polynucleotide or polypeptide of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Infectious Disease

A polypeptide or polynucleotide of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, the polypeptide or polynucleotide of the present invention may also directly inhibit the infectious agent, without necessarily eliciting an immune response.

Viruses are one example of an infectious agent that can cause disease or symptoms that can be treated or detected by a polynucleotide or polypeptide of the present invention. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillvirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. A polypeptide or polynucleotide of the present invention can be used to treat or detect any of these symptoms or diseases.

Similarly, bacterial or fungal agents that can cause disease or symptoms and that can be treated or detected by a polynucleotide or polypeptide of the present invention include, but not limited to, the following Gram-Negative and Gram-positive bacterial families and fungi: Actinomycetales (e.g., Corynebacterium, Mycobacterium, Norcardia), Aspergillosis, Bacillaceae (e.g., Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Klebsiella, Salmonella, Serratia, Yersinia), Erysipelothrix, Helicobacter, Legionellosis, Leptospirosis, Listeria, Mycoplasmatales, Neisseriaceae (e.g., Acinetobacter, Gonorrhea, Menigococcal), Pasteurellacea Infections (e.g., Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. A polypeptide or polynucleotide of the present invention can be used to treat or detect any of these symptoms or diseases.

Moreover, parasitic agents causing disease or symptoms that can be treated or detected by a polynucleotide or polypeptide of the present invention include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. A polypeptide or polynucleotide of the present invention can be used to treat or detect any of these symptoms or diseases.

Preferably, treatment using a polypeptide or polynucleotide of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide of the present invention may increase regeneration of tissues difficult to heal. For example, increased tendon/ligament regeneration would quicken recovery time after damage. A polynucleotide or polypeptide of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide of the present invention to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the polynucleotide or polypeptide of the present invention.

Chemotaxis

A polynucleotide or polypeptide of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that a polynucleotide or polypeptide of the present invention may inhibit chemotactic activity. These molecules could also be used to treat disorders. Thus, a polynucleotide or polypeptide of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., ligands and receptors),or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptide from suitably manipulated cells or tissues.

Therefore, the invention includes a method of identifying compounds which bind to a polypeptide of the invention comprising the steps of: (a) incubating a candidate binding compound with a polypeptide of the invention; and (b) determining if binding has occurred. Moreover, the invention includes a method of identifying agonists/antagonists comprising the steps of: (a) incubating a candidate compound with a polypeptide of the invention, (b) assaying a biological activity, and (b) determining if a biological activity of the polypeptide has been altered.

Other Activities

A polypeptide or polynucleotide of the present invention may also increase or decrease the differentiation or proliferation of embryonic stem cells, besides, as discussed above, hematopoietic lineage.

A polypeptide or polynucleotide of the present invention may also be used to modulate mammalian characteristics, such as body height, weight, hair color, eye color, skin, percentage of adipose tissue, pigmentation, size, and shape (e.g., cosmetic surgery). Similarly, a polypeptide or polynucleotide of the present invention may be used to modulate mammalian metabolism affecting catabolism, anabolism, processing, utilization, and storage of energy.

A polypeptide or polynucleotide of the present invention may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

A polypeptide or polynucleotide of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table 1, which DNA molecule is contained in the material deposited with the American Type Culture Collection and given the ATCC Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table 1, which DNA molecule is contained in the deposit given the ATCC Deposit Number shown in Table 1.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA containing the sequence of SEQ ID NO:X or contained in the ATCC deposited clones.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y (wherein Y is any integer as defined in Table 1).

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 7 contiguous amino acids in the complete amino acid sequence of a protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 30 contiguous amino acids in the amino acid sequence of protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 100 contiguous amino acids in the amino acid sequence of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to the amino acid sequence of the protein encoded by a human cDNA clone identified by a cDNA Clone Identifier in Table 1 and contained in the deposit with the ATCC Deposit Number shown for said cDNA clone in Table 1.

Further preferred is an isolated antibody which binds specifically to a polypeptide comprising an amino acid sequence that is at least 90% identical to a sequence of at least 7 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Further preferred is a method for detecting in a biological sample a polypeptide comprising an amino acid sequence which is at least 90% identical to a sequence of at least 7 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 7 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 7 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 7 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 7 contiguous amino acids in a sequence selected from the above group.

Also preferred is a method for diagnosing in a subject a pathological condition associated with abnormal structure or expression of a gene encoding a secreted protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 7 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 7 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a human protein comprising an amino acid sequence selected from the group consisting of: an amino acid sequence of SEQ ID NO:Y, and an amino acid sequence of a protein encoded by a human cDNA clone identified by a cDNA Clone Identifier in Table 1 and contained in the deposit with the ATCC Deposit Number shown for said cDNA clone in Table 1. The isolated polypeptide produced by this method is also preferred.

Also preferred is a method of treatment of an individual in need of an increased level of a protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

EXAMPLES

Example 1

Isolation of a Selected cDNA Clone From the Deposited Sample

Each cDNA clone in a cited ATCC deposit is contained in a pA2 plasmid vector (see Example 7). The deposited material in the sample assigned the ATCC Deposit Number cited in Table 1 contains all of the plasmids of Table 1. The ATCC deposit sample cited in Table 1 comprises a mixture of approximately equal amounts (by weight) of each different plasmid DNAs.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30–40 nucleotides is synthesized using an Applied Biosystems DNA synthesizer according to the sequence reported. The oligonucleotide is labeled, for instance, with $^{32}$P-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 μl of reaction mixture with 0.5 ug of the above cDNA template. A convenient reaction mixture is 1.5–5 mM $MgCl_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7):1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a-Polynucleotide

A human genomic P1 library (Genomic Systems, Inc.) is screened by PCR using primers selected for the cDNA sequence corresponding to SEQ ID NO:X., according to the method described in Example 1. (See also, Sambrook.)

Example 3

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70° C. overnight, and the films developed according to standard procedures.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds, 95° C.; 1 minute, 56° C.; 1 minute, 70° C. This cycle is repeated 32 times followed by one 5 minute cycle at 70° C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI and initiation/stop codons, if necessary, to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Amp'), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4,(Qiagen, Inc.) which contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000× g). The cell pellet is solubilized in the chaotropic agent 6 Molar Guanidine HCl by stirring for 34 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6× His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80 C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an E. coli origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide from an Inclusion Body

The following alternative method can be used to purify a polypeptide expressed in E coli when it is present in the form of inclusion bodies. Unless otherwise specified, all of the following steps are conducted at 4–10° C.

Upon completion of the production phase of the E. coli fermentation, the cell culture is cooled to 4–10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000× g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000× g centrifugation for 15 min., the pellet is discarded and the polypeptide containing supernatant is incubated at 4° C. overnight to allow further GuHCl extraction.

Following high speed centrifugation (30,000× g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 µg of purified protein is loaded. The purified protein can also be tested for endotoxin/LPS contamination, and typically the LPS content is less than 0.1 ng/ml according to LAL assays.

Example 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the cDNA sequence contained in the deposited clone is amplified using the PCR protocol described in Example 1 using primers with appropriate restriction sites and initiation/stop codons. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five µg of a plasmid containing the polynucleotide is co-transfected with 1.0 µg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One µg of BaculoGold™ virus DNA and 5 µg of the plasmid are mixed in a sterile well of a microtiter plate containing 50 µl of serum-free Grace's medium (Life Technologies Inc., Gaithersburg, Md.). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 µCi of $^{35}$S-methionine and 5 µCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1 using primers with appropriate restrictions sites and initiation/stop codons, if necessary. The vector can be modified to include a heterologous signal sequence if necessary for secretion. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five $\mu$g of the expression plasmid pC6 is cotransfected with 0.5 $\mu$g of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/mil G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 $\mu$M, 2 $\mu$M, 5 $\mu$M, 10 mM, 20 mM). The same procedure is repeated until clones are obtained which grow at a concentration of 100–200 $\mu$M. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EP A 394,827; Traunecker, et al., Nature 331:84–86 (1988)) The polypeptides can also be fused to heterologous polypeptide sequences to facilitate secretion and intracellular trafficking (e.g., KDEL). Moreover, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector, and initiation/stop codons, if necessary.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.) Human IgG Fc region:

spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The polypeptide is also suitably administered by sustained-release systems. Suitable examples of sustained-

```
GGGATCCGGAGCCCAAATCTTCTGACAAAACTCACACATGCCCACCGTGCCCA    (SEQ ID NO:1)

GCACCTGAATTCGAGGGTGCACCGTCAGTCTTCCTCTTCCCCCCAAAACCCAA

GGACACCCTCATGATCTCCCGGACTCCTGAGGTCACATGCGTGGTGGTGGACG

TAAGCCACGAAGACCCTGAGGTCAAGTTCAACTGGTACGTGGACGGCGTGGA

GGTGCATAATGCCAAGACAAAGCCGCGGGAGGAGCAGTACAACAGCACGTAC

CGTGTGGTCAGCGTCCTCACCGTCCTGCACCAGGACTGGCTGAATGGCAAGGA

GTACAAGTGCAAGGTCTCCAACAAAGCCCTCCCAACCCCCATCGAGAAAACC

ATCTCCAAAGCCAAAGGGCAGCCCCGAGAACCACAGGTGTACACCCTGCCCC

CATCCCGGGATGAGCTGACCAAGAACCAGGTCAGCCTGACCTGCCTGGTCAA

AGGCTTCTATCCAAGCGACATCGCCGTGGAGTGGGAGAGCAATGGGCAGCCG

GAGAACAACTACAAGACCACGCCTCCCGTGCTGGACTCCGACGGCTCCTTCTT

CCTCTACAGCAAGCTCACCGTGGACAAGAGCAGGTGGCAGCAGGGGAACGTC

TTCTCATGCTCCGTGATGCATGAGGCTCTGCACAACCACTACACGCAGAAGAG

CCTCTCCCTGTCTCCGGGTAAATGAGTGCGACGGCCGCGACTCTAGAGGAT
```

Example 10

Formulating a Polypeptide

The polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of polypeptide administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the polypeptide is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the polypeptide of the invention are administered orally, rectally, parenterally, intracisternally, intravaginally, intraperitoneally, topically (as by powders, ointments, gels, drops or transdermal patch), bucally, or as an oral or nasal release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly (2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(−)-3-hydroxybutyric acid (EP 133,988). Sustained-release compositions also include liposomally entrapped polypeptides. Liposomes containing the secreted polypeptide are prepared by methods known per se: DE 3,218,121; Epstein et al., Proc. Natl. Acad. Sci. USA 82:3688–3692 (1985); Hwang et al., Proc. Natl. Acad. Sci. USA 77:40304034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, the polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, seated ampoules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Example 11

Method of Treating Decreased Levels of the Polypeptide

It will be appreciated that conditions caused by a decrease in the standard or normal expression level of a polypeptide in an individual can be treated by administering the polypeptide of the present invention, preferably in the secreted and/or soluble form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided in Example 10.

Example 12

Method of Treating Increased Levels of the Polypeptide

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 10.

Example 13

Method of Treatment Using Gene Therapy

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB 101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated nucleic acid molecule comprising a polynucleotide selected from the group consisting of:
   (a) a polynucleotide encoding amino acid residues 1 to 434 of SEQ ID NO:2; and
   (b) a polynucleotide encoding amino acid residues 2 to 434 of SEQ ID NO:2.

2. The isolated nucleic acid molecule of claim 1, wherein said polynucleotide is (a).

3. The isolated nucleic acid molecule of claim 1, wherein said polynucleotide is (b).

4. The isolated nucleic acid molecule of claim 1, wherein the polynucleotide further comprises a heterologous polynucleotide.

5. The isolated nucleic acid molecule of claim 4, wherein said heterologous polynucleotide encodes a heterologous polypeptide.

6. A recombinant vector comprising the isolated nucleic acid molecule of claim 1.

7. The recombinant vector of claim 6, wherein the nucleic acid molecule is operably associated with a heterologous regulatory sequence that controls gene expression.

8. A method of producing a recombinant vector comprising inserting the isolated nucleic acid molecule of claim 1 into a vector.

9. A recombinant host cell comprising the isolated nucleic acid molecule of claim 1.

10. The recombinant host cell of claim 9, wherein the nucleic acid molecule is operably associated with a heterologous regulatory sequence that controls gene expression.

11. A recombinant host cell comprising the recombinant vector of claim 6.

12. A method of producing a host cell comprising transducing, transforming or transfecting a host cell with the vector of claim 6.

13. A method for producing a protein, comprising:
   (a) culturing the host cell of claim 9 under conditions suitable to produce the polypeptide encoded by said nucleic acid molecule; and
   (b) recovering the protein from the cell culture.

14. An isolated nucleic acid molecule comprising a polynucleotide selected from the group consisting of:
   (a) a polynucleotide encoding the amino acid sequence of the full-length CMP Sialic Acid Synthetase (CMP-SAS) polypeptide, which amino acid sequence is encoded by the HWLLM34 cDNA clone contained in ATCC Deposit No. PTA-1410; and
   (b) a polynucleotide encoding the amino acid sequence of the full-length CMP-SAS polypeptide, excluding the N-terminal methionine residue, which amino acid sequence is encoded by the HWLLM34 cDNA clone contained in ATCC Deposit No. PTA-1410.

15. The isolated nucleic acid molecule of claim 14, wherein said polynucleotide is (a).

16. The isolated nucleic acid molecule of claim 14, wherein said polynucleotide is (b).

17. The isolated nucleic acid molecule of claim 14, wherein the polynucleotide further comprises a heterologous polynucleotide.

18. The isolated nucleic acid molecule of claim 17, wherein said heterologous polynucleotide encodes a heterologous polypeptide.

19. A recombinant vector comprising the isolated nucleic acid molecule of claim 14.

20. The recombinant vector of claim 19, wherein the nucleic acid molecule is operably associated with a heterologous regulatory sequence that controls gene expression.

21. A method of producing a recombinant vector comprising inserting the isolated nucleic acid molecule of claim 14 into a vector.

22. A recombinant host cell comprising the isolated nucleic acid molecule of claim 14.

23. The recombinant host cell of claim 22, wherein the nucleic acid molecule is operably associated with a heterologous regulatory sequence that controls gene expression.

24. A recombinant host cell comprising the recombinant vector of claim 19.

25. A method of producing a host cell comprising transducing, transforming or transfecting a host cell with the vector of claim 19.

26. A method for producing a protein, comprising:
  (a) culturing the host cell of claim 23 under conditions suitable to produce the polypeptide encoded by said nucleic acid molecule; and
  (b) recovering the protein from the cell culture.

27. An isolated nucleic acid molecule comprising a polynucleotide encoding a first polypeptide 90% or more identical to a second polypeptide selected from the group consisting of:
  (a) amino acid residues 1 to 434 of SEQ ID NO:2; and
  (b) amino acid residues 2 to 434 of SEQ ID NO:2,
wherein said first polypeptide has CMP-SAS activity or specifically binds an antibody that specifically binds the polypeptide of SEQ ID NO:2.

28. The isolated nucleic acid molecule of claim 27, wherein said second polypeptide is (a).

29. The isolated nucleic acid molecule of claim 27, wherein said second polypeptide is (b).

30. The isolated nucleic acid molecule of claim 27 which comprises a polynucleotide encoding a first polypeptide 95% or more identical to a second polypeptide consisting of amino acid residues 1 to 434 of SEQ ID NO:2.

31. The isolated nucleic acid molecule of claim 27 which comprises a polynucleotide encoding a first polypeptide 95% or more identical to a second polypeptide consisting of amino acid residues 2 to 434 of SEQ ID NO:2.

32. The isolated nucleic acid molecule of claim 27, wherein the polynucleotide further comprises a heterologous polynucleotide.

33. The isolated nucleic acid molecule of claim 32, wherein said heterologous polynucleotide encodes a heterologous polypeptide.

34. A recombinant vector comprising the isolated nucleic acid molecule of claim 27.

35. The recombinant vector of claim 34, wherein the nucleic acid molecule is operably associated with a heterologous regulatory sequence that controls gene expression.

36. A method of producing a recombinant vector comprising inserting the isolated nucleic acid molecule of claim 27 into a vector.

37. A recombinant host cell comprising the isolated nucleic acid molecule of claim 27.

38. The recombinant host cell of claim 37, wherein the nucleic acid molecule is operably associated with a heterologous regulatory sequence that controls gene expression.

39. A recombinant host cell comprising the recombinant vector of claim 34.

40. A method of producing a host cell comprising transducing, transforming or transfecting a host cell with the vector of claim 34.

41. A method for producing a protein, comprising:
  (a) culturing the host cell of claim 38 under conditions suitable to produce the polypeptide encoded by said nucleic acid molecule; and
  (b) recovering the protein from the cell culture.

42. An isolated nucleic acid molecule comprising a polynucleotide encoding a first polypeptide 90% or more identical to a second polypeptide selected from the group consisting of:
  (a) the full-length CMP-SAS polypeptide as encoded by the HWLLM34 cDNA clone contained in ATCC Deposit No. PTA-1410; and
  (b) the full-length CMP-SAS polypeptide, excluding the N-terminal methionine residue as encoded by the HWLLM34 cDNA clone contained in ATCC Deposit No. PTA-1410,
wherein said first polypeptide has CMP-SAS activity or specifically binds an antibody that specifically binds the polypeptide of SEQ ID NO:2.

43. The isolated nucleic acid molecule of claim 42, wherein said second polypeptide is (a).

44. The isolated nucleic acid molecule of claim 42, wherein said second polypeptide is (b).

45. The isolated nucleic acid molecule of claim 42 which comprises a polynucleotide encoding a first polypeptide 95% or more identical to the full-length CMP-SAS polypeptide as encoded by the HWLLM34 cDNA clone contained in ATCC Deposit No. PTA-1410.

46. The isolated nucleic acid molecule of claim 42 which comprises a polynucleotide encoding a first polypeptide 95% or more identical to the full-length CMP-SAS polypeptide, excluding the N-terminal methionine residue as encoded by the HWLLM34 cDNA clone contained in ATCC Deposit No. PTA-1410.

47. The isolated nucleic acid molecule of claim 42, wherein the polynucleotide further comprises a heterologous polynucleotide.

48. The isolated nucleic acid molecule of claim 47, wherein said heterologous polynucleotide encodes a heterologous polypeptide.

49. A recombinant vector comprising the isolated nucleic acid molecule of claim 42.

50. The recombinant vector of claim 49, wherein the nucleic acid molecule is operably associated with a heterologous regulatory sequence that controls gene expression.

51. A method of producing a recombinant vector comprising inserting the isolated nucleic acid molecule of claim 42 into a vector.

52. A recombinant host cell comprising the isolated nucleic acid molecule of claim 42.

53. The recombinant host cell of claim 52, wherein the nucleic acid molecule is operably associated with a heterologous regulatory sequence that controls gene expression.

54. A recombinant host cell comprising the recombinant vector of claim 49.

55. A method of producing a host cell comprising transducing, transforming or transfecting a host cell with the vector of claim 49.

56. A method for producing a protein, comprising:
(a) culturing the host cell of claim 53 under conditions suitable to produce the polypeptide encoded by said nucleic acid molecule; and
(b) recovering the protein from the cell culture.

57. An isolated nucleic acid molecule comprising a polynucleotide fragment encoding a fragment of SEQ ID NO:2 with CMP-SAS.

58. The isolated nucleic acid molecule of claim 57, wherein the polynucleotide further comprises a heterologous polynucleotide.

59. The isolated nucleic acid molecule of claim 58, wherein said heterologous polynucleotide encodes a heterologous polypeptide.

60. A recombinant vector comprising the isolated nucleic acid molecule of claim 57.

61. The recombinant vector of claim 60, wherein the nucleic acid molecule is operably associated with a heterologous regulatory sequence that controls expression of said fragment.

62. A method of producing a recombinant vector comprising inserting the isolated nucleic acid molecule of claim 57 into a vector.

63. A recombinant host cell comprising the isolated nucleic acid molecule of claim 57.

64. The recombinant host cell of claim 63, wherein the nucleic acid molecule is operably associated with a heterologous regulatory sequence that controls gene expression.

65. A recombinant host cell comprising the recombinant vector of claim 60.

66. A method of producing a host cell comprising transducing, transforming or transfecting a host cell with the vector of claim 60.

67. A method for producing a protein, comprising:
(a) culturing the host cell of claim 64 under conditions suitable to produce the polypeptide encoded by said nucleic acid molecule; and
(b) recovering the protein from the cell culture.

68. An isolated nucleic acid molecule comprising a polynucleotide fragment encoding a fragment of the polypeptide encoded by the HWLLM34 cDNA clone contained in ATCC Deposit No. PTA-1410, wherein said fragment has CMP-sialic acid synthetase activity.

69. The isolated nucleic acid molecule of claim 68, wherein the polynucleotide further comprises a heterologous polynucleotide.

70. The isolated nucleic acid molecule of claim 69, wherein said heterologous polynucleotide encodes a heterologous polypeptide.

71. A recombinant vector comprising the isolated nucleic acid molecule of claim 68.

72. The recombinant vector of claim 71, wherein the nucleic acid molecule is operably associated with a heterologous regulatory sequence that controls expression of said fragment.

73. A method of producing a recombinant vector comprising inserting the isolated nucleic acid molecule of claim 68 into a vector.

74. A recombinant host cell comprising the isolated nucleic acid molecule of claim 68.

75. The recombinant host cell of claim 74, wherein the nucleic acid molecule is operably associated with a heterologous regulatory sequence that controls gene expression.

76. A recombinant host cell comprising the recombinant vector of claim 71.

77. A method of producing a host cell comprising transducing, transforming or transfecting a host cell with the vector of claim 71.

78. A method for producing a protein, comprising:
(a) culturing the host cell of claim 75 under conditions suitable to produce the polypeptide encoded by said nucleic acid molecule; and
(b) recovering the protein from the cell culture.

79. A nucleic acid fragment comprising a polynucleotide encoding a fragment of SEQ ID NO:2, having CMP-SAS activity.

80. The nucleic acid fragment of claim 79, wherein the polynucleotide further comprises a heterologous polynucleotide.

81. The isolated nucleic acid molecule of claim 80, wherein said heterologous polynucleotide encodes a heterologous polypeptide.

82. A recombinant vector comprising the isolated nucleic acid molecule of claim 79.

83. A method of producing a recombinant vector comprising inserting the isolated nucleic acid molecule of claim 79 into a vector.

84. A recombinant host cell comprising the isolated nucleic acid molecule of claim 79.

85. A recombinant host cell comprising the recombinant vector of claim 82.

86. A method of producing a host cell comprising transducing, transforming or transfecting a host cell with the vector of claim 82.

87. A method for producing a protein comprising:
(a) culturing the host cell of claim 84 under conditions suitable to produce the polypeptide encoded by said nucleic acid molecule; and
(b) recovering the protein from the cell culture.

88. A nucleic acid fragment comprising a polynucleotide encoding a fragment of the polypeptide having CMP-SAS activity encoded by the HWLLM34 cDNA clone contained in ATCC Deposit No. PTA-1410, wherein said polynucleotide is operatively associated with a regulatory element to direct expression of said polypeptide fragment.

89. The nucleic acid fragment of claim 88, wherein the polynucleotide further comprises a heterologous polynucleotide.

90. The nucleic acid fragment of claim 89, wherein said heterologous polynucleotide encodes a heterologous polypeptide.

91. A recombinant vector comprising the isolated nucleic acid fragment of claim 88.

92. A method of producing a recombinant vector comprising inserting the isolated nucleic acid fragment of claim 88 into a vector.

93. A recombinant host cell comprising the nucleic acid fragment of claim 88.

94. A recombinant host cell comprising the recombinant vector of claim 91.

95. A method of producing a host cell comprising transducing, transforming or transfecting a host cell with the vector of claim 91.

96. A method for producing a protein, comprising:
(a) culturing the host cell of claim 93 under conditions suitable to produce the polypeptide encoded by said nucleic acid fragment; and
(b) recovering the protein from the cell culture.

97. An isolated polynucleotide comprising a polynucleotide which hybridizes to the complement of the polynucleotide set forth in SEQ ID NO:1 wherein under conditions of hybridization in a buffer consisting of 50% formamide, 5× SSC, 50 mM sodium phosphate (pH 7.6), 5× Denhardt's solution, 10% dextran sulfate, and 20 µg/ml denatured, sheared salmon sperm DNA at 42° C. and wash in a solution consisting of 0.1× SSC at 65° C.; wherein said polynucleotide encodes a polypeptide with CMP-sialic acid synthetase activity.

98. The isolated nucleic acid molecule of claim 97, wherein the polynucleotide further comprises a heterologous polynucleotide.

99. The isolated nucleic acid molecule of claim 98, wherein said heterologous polynucleotide encodes a heterologous polypeptide.

100. A recombinant vector comprising the isolated nucleic acid molecule of claim 97.

101. The recombinant vector of claim 100, wherein the nucleic acid molecule is operably associated with a heterologous regulatory sequence that controls gene expression.

102. A method of producing a recombinant vector comprising inserting the isolated nucleic acid molecule of claim 97, into a vector.

103. A recombinant host cell comprising the isolated nucleic acid molecule of claim 97.

104. The recombinant host cell of claim 103, wherein the nucleic acid molecule is operably associated with a heterologous regulatory sequence that controls gene expression.

105. A recombinant host cell comprising the recombinant vector of claim 100.

106. A method of producing a host cell comprising transducing, transforming or transfecting a host cell with the vector of claim 100.

107. A method for producing a protein, comprising:
(a) culturing the host cell of claim 104 under conditions suitable to produce the polypeptide encoded by said nucleic acid molecule; and
(b) recovering the protein from the cell culture.

108. An isolated polynucleotide comprising a polynucleotide which hybridizes to the complement of the CMP-sialic acid synthetase coding sequence of the HWLLM34 cDNA clone contained in ATCC Deposit No. PTA-1410 under conditions of hybridization in a buffer consisting of 50% formamide, 5× SSC, 50 mM sodium phosphate (pH 7.6), 5× Denhardt's solution, 10% dextran sulfate, and 20 µg/ml denatured, sheared salmon sperm DNA at 42° C. and wash in a solution consisting of 0.1× SSC at 65° C.; wherein said polynucleotide encodes a polypeptide with CMP-sialic acid synthetase activity.

109. The isolated nucleic acid molecule of claim 108, wherein the polynucleotide further comprises a heterologous polynucleotide.

110. The isolated nucleic acid molecule of claim 109, wherein said heterologous polynucleotide encodes a heterologous polypeptide.

111. A recombinant vector comprising the isolated nucleic acid molecule of claim 108.

112. The recombinant vector of claim 111, wherein the nucleic acid molecule is operably associated with a heterologous regulatory sequence that controls gene expression.

113. A method of producing a recombinant vector comprising inserting the isolated nucleic acid molecule of claim 108 into a vector.

114. A recombinant host cell comprising the isolated nucleic acid molecule of claim 108.

115. The recombinant host cell of claim 114, wherein the nucleic acid molecule is operably associated with a heterologous regulatory sequence that controls gene expression.

116. A recombinant host cell comprising the recombinant vector of claim 111.

117. A method of producing a host cell comprising transducing, transforming or transfecting a host cell with the vector of claim 111.

118. A method for producing a protein, comprising:
(a) culturing the host cell of claim 115 under conditions suitable to produce the polypeptide encoded by said nucleic acid molecule; and
(b) recovering the protein from the cell culture.

* * * * *

UNITED STATES PATENT AND TRADEMARK OFFICE
CERTIFICATE OF CORRECTION

PATENT NO. : 6,783,971 B2
DATED : August 31, 2004
INVENTOR(S) : Coleman et al.

It is certified that error appears in the above-identified patent and that said Letters Patent is hereby corrected as shown below:

Column 85,
Line 11, insert -- activity. -- after "CMP-SAS".

Column 86,
Line 12, insert the phrase "wherein said polynucleotide is operatively associated with a regulatory element to direct expression of said polypeptide fragment." after "CMP-SAS activity".

Signed and Sealed this

Fifth Day of April, 2005

JON W. DUDAS
*Director of the United States Patent and Trademark Office*

SEQUENCE LISTING

```
<160> NUMBER OF SEQ ID NOS: 6

<210> SEQ ID NO 1
<211> LENGTH: 1305
<212> TYPE: DNA
<213> ORGANISM: Homo sapiens
<220> FEATURE:
<221> NAME/KEY: CDS
<222> LOCATION: (1)..(1302)
<221> NAME/KEY: SITE
<222> LOCATION: (397)..(399)
<223> OTHER INFORMATION: yat encodes Tyr or His
<221> NAME/KEY: SITE
<222> LOCATION: (406)..(408)
<223> OTHER INFORMATION: gkt encodes Gly or Val
<221> NAME/KEY: SITE
<222> LOCATION: (439)..(441)
<223> OTHER INFORMATION: yca encodes Ser or Pro
<221> NAME/KEY: SITE
<222> LOCATION: (505)..(507)
<223> OTHER INFORMATION: gkt encodes Gly or Val

<400> SEQUENCE: 1 atg gac tcg gtg gag aag ggg gcc gcc acc tcc gtc tcc aac ccg cgg      48
Met Asp Ser Val Glu Lys Gly Ala Ala Thr Ser Val Ser Asn Pro Arg
 1               5                  10                  15 ggg cga ccg tcc cgg ggc cgg ccg ccg aag ctg cag cgc aac tct cgc      96
Gly Arg Pro Ser Arg Gly Arg Pro Pro Lys Leu Gln Arg Asn Ser Arg
             20                  25                  30 ggc ggc cag ggc cga ggt gtg gag aag ccc ccg cac ctg gca gcc cta     144
Gly Gly Gln Gly Arg Gly Val Glu Lys Pro Pro His Leu Ala Ala Leu
         35                  40                  45 att ctg gcc cgg gga ggc agc aaa ggc atc ccc ctg aag aac att aag     192
Ile Leu Ala Arg Gly Gly Ser Lys Gly Ile Pro Leu Lys Asn Ile Lys
     50                  55                  60 cac ctg gcg ggg gtc ccg ctc att ggc tgg gtc ctg cgt gcg gcc ctg     240
His Leu Ala Gly Val Pro Leu Ile Gly Trp Val Leu Arg Ala Ala Leu
 65                  70                  75                  80
```

```
                                                         -continued gat tca ggg gcc ttc cag agt gta tgg gtt tcg aca gac cat gat gaa     288
Asp Ser Gly Ala Phe Gln Ser Val Trp Val Ser Thr Asp His Asp Glu
                85                  90                  95 att gag aat gtg gcc aaa caa ttt ggt gca caa gtt cat cga aga agt     336
Ile Glu Asn Val Ala Lys Gln Phe Gly Ala Gln Val His Arg Arg Ser
            100                 105                 110 tct gaa gtt tca aaa gac agc tct acc tca cta gat gcc atc ata gaa     384
Ser Glu Val Ser Lys Asp Ser Ser Thr Ser Leu Asp Ala Ile Ile Glu
        115                 120                 125 ttt ctt aat tat yat aat gag gkt gac att gta gga aat att caa gct     432
Phe Leu Asn Tyr Xaa Asn Glu Xaa Asp Ile Val Gly Asn Ile Gln Ala
    130                 135                 140 act tct yca tgt tta cat cct act gat ctt caa aaa gtt gca gaa atg     480
Thr Ser Xaa Cys Leu His Pro Thr Asp Leu Gln Lys Val Ala Glu Met
145                 150                 155                 160 att cga gaa gaa gga tat gat tct gkt ttc tct gtt gtg aga cgc cat     528
Ile Arg Glu Glu Gly Tyr Asp Ser Xaa Phe Ser Val Val Arg Arg His
                165                 170                 175 cag ttt cga tgg agt gaa att cag aaa gga gtt cgt gaa gtg acc gaa     576
Gln Phe Arg Trp Ser Glu Ile Gln Lys Gly Val Arg Glu Val Thr Glu
            180                 185                 190 cct ctg aat tta aat cca gct aaa cgg cct cgt cga caa gac tgg gat     624
Pro Leu Asn Leu Asn Pro Ala Lys Arg Pro Arg Arg Gln Asp Trp Asp
        195                 200                 205 gga gaa tta tat gaa aat ggc tca ttt tat ttt gct aaa aga cat ttg     672
Gly Glu Leu Tyr Glu Asn Gly Ser Phe Tyr Phe Ala Lys Arg His Leu
    210                 215                 220 ata gag atg ggt tac ttg cag ggt gga aaa tgg cat act acg aaa tgc     720
Ile Glu Met Gly Tyr Leu Gln Gly Gly Lys Trp His Thr Thr Lys Cys
225                 230                 235                 240 gag ctg gaa cat agt gtg gat ata gat gtg gat att gat tgg cct att     768
Glu Leu Glu His Ser Val Asp Ile Asp Val Asp Ile Asp Trp Pro Ile
                245                 250                 255 gca gag caa aga gta tta aga tat ggc tat ttt ggc aaa gag aag ctt     816
Ala Glu Gln Arg Val Leu Arg Tyr Gly Tyr Phe Gly Lys Glu Lys Leu
            260                 265                 270 aag gaa ata aaa ctt ttg gtt tgc aat att gat gga tgt ctc acc aat     864
Lys Glu Ile Lys Leu Leu Val Cys Asn Ile Asp Gly Cys Leu Thr Asn
        275                 280                 285 ggc cac att tat gta tca gga gac caa aaa gaa ata ata tct tat gat     912
Gly His Ile Tyr Val Ser Gly Asp Gln Lys Glu Ile Ile Ser Tyr Asp
    290                 295                 300 gta aaa gat gct att ggg ata agt tta tta aag aaa agt ggt att gag     960
Val Lys Asp Ala Ile Gly Ile Ser Leu Leu Lys Lys Ser Gly Ile Glu
305                 310                 315                 320 gtg agg cta atc tca gaa agg gcc tgt tca aag cag acg ctg tct tct    1008
Val Arg Leu Ile Ser Glu Arg Ala Cys Ser Lys Gln Thr Leu Ser Ser
                325                 330                 335 tta aaa ctg gat tgc aaa atg gaa gtc agt gta tca gac aag cta gca    1056
Leu Lys Leu Asp Cys Lys Met Glu Val Ser Val Ser Asp Lys Leu Ala
            340                 345                 350 gtt gta gat gaa tgg aga aaa gaa atg ggc ctg tgc tgg aaa gaa gtg    1104
Val Val Asp Glu Trp Arg Lys Glu Met Gly Leu Cys Trp Lys Glu Val
        355                 360                 365 gca tat ctt gga aat gaa gtg tct gat gaa gag tgc ttg aag aga gtg    1152
Ala Tyr Leu Gly Asn Glu Val Ser Asp Glu Glu Cys Leu Lys Arg Val
    370                 375                 380 ggc cta agt ggc gct cct gct gat gcc tgt tcc tac gcc cag aag gct    1200
Gly Leu Ser Gly Ala Pro Ala Asp Ala Cys Ser Tyr Ala Gln Lys Ala
385                 390                 395                 400
```

-continued

```
gtt gga tac att tgc aaa tgt aat ggt ggc cgt ggt gcc atc cga gaa    1248
Val Gly Tyr Ile Cys Lys Cys Asn Gly Gly Arg Gly Ala Ile Arg Glu
                405                 410                 415 ttt gca gag cac att tgc cta cta atg gaa aaa gtt aat aat tca tgc    1296
Phe Ala Glu His Ile Cys Leu Leu Met Glu Lys Val Asn Asn Ser Cys
            420                 425                 430 caa aaa tag                                                         1305
Gln Lys
```

<210> SEQ ID NO 2
<211> LENGTH: 434
<212> TYPE: PRT
<213> ORGANISM: Homo sapiens
<220> FEATURE:
<221> NAME/KEY: SITE
<222> LOCATION: 133
<223> OTHER INFORMATION: Xaa equals Tyr or His
<221> NAME/KEY: SITE
<222> LOCATION: 136
<223> OTHER INFORMATION: Xaa equals Gly or Val
<221> NAME/KEY: SITE
<222> LOCATION: 147
<223> OTHER INFORMATION: Xaa equals Ser or Pro
<221> NAME/KEY: SITE
<222> LOCATION: 169
<223> OTHER INFORMATION: Xaa equals Gly or Val

<400> SEQUENCE: 2

```
Met Asp Ser Val Glu Lys Gly Ala Ala Thr Ser Val Ser Asn Pro Arg
  1               5                  10                  15

Gly Arg Pro Ser Arg Gly Arg Pro Lys Leu Gln Arg Asn Ser Arg
                 20                  25                  30

Gly Gly Gln Gly Arg Gly Val Glu Lys Pro Pro His Leu Ala Ala Leu
             35                  40                  45

Ile Leu Ala Arg Gly Gly Ser Lys Gly Ile Pro Leu Lys Asn Ile Lys
         50                  55                  60

His Leu Ala Gly Val Pro Leu Ile Gly Trp Val Leu Arg Ala Ala Leu
 65                  70                  75                  80

Asp Ser Gly Ala Phe Gln Ser Val Trp Val Ser Thr Asp His Asp Glu
                 85                  90                  95

Ile Glu Asn Val Ala Lys Gln Phe Gly Ala Gln Val His Arg Arg Ser
            100                 105                 110

Ser Glu Val Ser Lys Asp Ser Thr Ser Leu Asp Ala Ile Ile Glu
        115                 120                 125

Phe Leu Asn Tyr Xaa Asn Glu Xaa Asp Ile Val Gly Asn Ile Gln Ala
130                 135                 140

Thr Ser Xaa Cys Leu His Pro Thr Asp Leu Gln Lys Val Ala Glu Met
145                 150                 155                 160

Ile Arg Glu Glu Gly Tyr Asp Ser Xaa Phe Ser Val Val Arg His
                165                 170                 175

Gln Phe Arg Trp Ser Glu Ile Gln Lys Gly Val Arg Glu Val Thr Glu
            180                 185                 190

Pro Leu Asn Leu Asn Pro Ala Lys Arg Pro Arg Arg Gln Asp Trp Asp
        195                 200                 205

Gly Glu Leu Tyr Glu Asn Gly Ser Phe Tyr Phe Ala Lys Arg His Leu
    210                 215                 220

Ile Glu Met Gly Tyr Leu Gln Gly Gly Lys Trp His Thr Thr Lys Cys
225                 230                 235                 240

Glu Leu Glu His Ser Val Asp Ile Asp Val Asp Ile Asp Trp Pro Ile
```

-continued

```
                    245                 250                 255
Ala Glu Gln Arg Val Leu Arg Tyr Gly Tyr Phe Gly Lys Glu Lys Leu
            260                 265                 270
Lys Glu Ile Lys Leu Leu Val Cys Asn Ile Asp Gly Cys Leu Thr Asn
                275                 280                 285
Gly His Ile Tyr Val Ser Gly Asp Gln Lys Glu Ile Ser Tyr Asp
        290                 295                 300
Val Lys Asp Ala Ile Gly Ile Ser Leu Leu Lys Lys Ser Gly Ile Glu
305                 310                 315                 320
Val Arg Leu Ile Ser Glu Arg Ala Cys Ser Lys Gln Thr Leu Ser Ser
                325                 330                 335
Leu Lys Leu Asp Cys Lys Met Glu Val Ser Val Ser Asp Lys Leu Ala
            340                 345                 350
Val Val Asp Glu Trp Arg Lys Glu Met Gly Leu Cys Trp Lys Glu Val
                355                 360                 365
Ala Tyr Leu Gly Asn Glu Val Ser Asp Glu Glu Cys Leu Lys Arg Val
        370                 375                 380
Gly Leu Ser Gly Ala Pro Ala Asp Ala Cys Ser Tyr Ala Gln Lys Ala
385                 390                 395                 400
Val Gly Tyr Ile Cys Lys Cys Asn Gly Gly Arg Gly Ala Ile Arg Glu
                405                 410                 415
Phe Ala Glu His Ile Cys Leu Leu Met Glu Lys Val Asn Asn Ser Cys
            420                 425                 430
Gln Lys
```

<210> SEQ ID NO 3
<211> LENGTH: 1080
<212> TYPE: DNA
<213> ORGANISM: Homo sapiens
<220> FEATURE:
<221> NAME/KEY: CDS
<222> LOCATION: (1)..(1077)

<400> SEQUENCE: 3

```
atg ccg ctg gag ctg gag ctg tgt ccc ggg cgc tgg gtg ggc ggg caa     48
Met Pro Leu Glu Leu Glu Leu Cys Pro Gly Arg Trp Val Gly Gly Gln
  1               5                  10                  15 cac ccg tgc ttc atc att gcc gag atc ggc cag aac cac cag ggc gac     96
His Pro Cys Phe Ile Ile Ala Glu Ile Gly Gln Asn His Gln Gly Asp
                 20                  25                  30 ctg gac gta gcc aag cgc atg atc cgc atg gcc aag gag tgt ggg gct    144
Leu Asp Val Ala Lys Arg Met Ile Arg Met Ala Lys Glu Cys Gly Ala
             35                  40                  45 gat tgt gcc aag ttc cag aag agt gag cta gaa ttc aag ttt aat cgg    192
Asp Cys Ala Lys Phe Gln Lys Ser Glu Leu Glu Phe Lys Phe Asn Arg
         50                  55                  60 aaa gcc ttg gag agg cca tac acc tcg aag cat tcc tgg ggg aag acg    240
Lys Ala Leu Glu Arg Pro Tyr Thr Ser Lys His Ser Trp Gly Lys Thr
 65                  70                  75                  80 tac ggg gag cac aaa cga cat ctg gag ttc agc cat gac cag tac agg    288
Tyr Gly Glu His Lys Arg His Leu Glu Phe Ser His Asp Gln Tyr Arg
                 85                  90                  95 gag ctg cag agg tac gcc gag gag gtt ggg atc ttc ttc act gcc tct    336
Glu Leu Gln Arg Tyr Ala Glu Glu Val Gly Ile Phe Phe Thr Ala Ser
                100                 105                 110 ggc atg gat gag atg gca gtt gaa ttc ctg cat gaa ctg aat gtt cca    384
Gly Met Asp Glu Met Ala Val Glu Phe Leu His Glu Leu Asn Val Pro
            115                 120                 125
```

-continued

```
ttt ttc aaa gtt gga tct gga gac act aat aat ttt cct tat ctg gaa      432
Phe Phe Lys Val Gly Ser Gly Asp Thr Asn Asn Phe Pro Tyr Leu Glu
    130                 135                 140 aag aca gcc aaa aaa ggt cgc cca atg gtg atc tcc agt ggg atg cag      480
Lys Thr Ala Lys Lys Gly Arg Pro Met Val Ile Ser Ser Gly Met Gln
145                 150                 155                 160 tca atg gac acc atg aag caa gtt tat cag atc gtg aag ccc ctc aac      528
Ser Met Asp Thr Met Lys Gln Val Tyr Gln Ile Val Lys Pro Leu Asn
                165                 170                 175 ccc aac ttc tgc ttc ttg cag tgt acc agc gca tac ccg ctc cag cct      576
Pro Asn Phe Cys Phe Leu Gln Cys Thr Ser Ala Tyr Pro Leu Gln Pro
            180                 185                 190 gag gac gtc aac ctg cgg gtc atc tcg gaa tat cag aag ctc ttt cct      624
Glu Asp Val Asn Leu Arg Val Ile Ser Glu Tyr Gln Lys Leu Phe Pro
        195                 200                 205 gac att ccc ata ggg tat tct ggg cat gaa aca ggc ata gcg ata tct      672
Asp Ile Pro Ile Gly Tyr Ser Gly His Glu Thr Gly Ile Ala Ile Ser
    210                 215                 220 gtg gcc gca gtg gct ctg ggg gcc aag gtg ttg gaa cgt cac ata act      720
Val Ala Ala Val Ala Leu Gly Ala Lys Val Leu Glu Arg His Ile Thr
225                 230                 235                 240 ttg gac aag acc tgg aag ggg agt gac cac tcg gcc tcg ctg gag cct      768
Leu Asp Lys Thr Trp Lys Gly Ser Asp His Ser Ala Ser Leu Glu Pro
                245                 250                 255 gga gaa ctg gcc gag ctg gtg cgg tca gtg cgt ctt gtg gag cgt gcc      816
Gly Glu Leu Ala Glu Leu Val Arg Ser Val Arg Leu Val Glu Arg Ala
            260                 265                 270 ctg ggc tcc cca acc aag cag ctg ctg ccc tgt gag atg gcc tgc aat      864
Leu Gly Ser Pro Thr Lys Gln Leu Leu Pro Cys Glu Met Ala Cys Asn
        275                 280                 285 gag aag ctg ggc aag tct gtg gtg gcc aaa gtg aaa att ccg gaa ggc      912
Glu Lys Leu Gly Lys Ser Val Val Ala Lys Val Lys Ile Pro Glu Gly
    290                 295                 300 acc att cta aca atg gac atg ctc acc gtg aag gtg ggt gag ccc aaa      960
Thr Ile Leu Thr Met Asp Met Leu Thr Val Lys Val Gly Glu Pro Lys
305                 310                 315                 320 gcc tat cct cct gaa gac atc ttt aat cta gtg ggc aag aag gtc ctg     1008
Ala Tyr Pro Pro Glu Asp Ile Phe Asn Leu Val Gly Lys Lys Val Leu
                325                 330                 335 gtc act gtt gaa gag gat gac acc atc atg gaa gaa ttg gta gat aat     1056
Val Thr Val Glu Glu Asp Asp Thr Ile Met Glu Glu Leu Val Asp Asn
            340                 345                 350 cat ggc aaa aaa atc aag tct taa                                     1080
His Gly Lys Lys Ile Lys Ser
        355

<210> SEQ ID NO 4
<211> LENGTH: 359
<212> TYPE: PRT
<213> ORGANISM: Homo sapiens

<400> SEQUENCE: 4

Met Pro Leu Glu Leu Glu Leu Cys Pro Gly Arg Trp Val Gly Gly Gln
1               5                   10                  15

His Pro Cys Phe Ile Ile Ala Glu Ile Gly Gln Asn His Gln Gly Asp
            20                  25                  30

Leu Asp Val Ala Lys Arg Met Ile Arg Met Ala Lys Glu Cys Gly Ala
        35                  40                  45

Asp Cys Ala Lys Phe Gln Lys Ser Glu Leu Glu Phe Lys Phe Asn Arg
```

```
                50                   55                   60
Lys Ala Leu Glu Arg Pro Tyr Thr Ser Lys His Ser Trp Gly Lys Thr
 65                  70                  75                  80

Tyr Gly Glu His Lys Arg His Leu Glu Phe Ser His Asp Gln Tyr Arg
                 85                  90                  95

Glu Leu Gln Arg Tyr Ala Glu Val Gly Ile Phe Phe Thr Ala Ser
            100                 105                 110

Gly Met Asp Glu Met Ala Val Glu Phe Leu His Glu Leu Asn Val Pro
            115                 120                 125

Phe Phe Lys Val Gly Ser Gly Asp Thr Asn Asn Phe Pro Tyr Leu Glu
130                 135                 140

Lys Thr Ala Lys Lys Gly Arg Pro Met Val Ile Ser Ser Gly Met Gln
145                 150                 155                 160

Ser Met Asp Thr Met Lys Gln Val Tyr Gln Ile Val Lys Pro Leu Asn
                165                 170                 175

Pro Asn Phe Cys Phe Leu Gln Cys Thr Ser Ala Tyr Pro Leu Gln Pro
            180                 185                 190

Glu Asp Val Asn Leu Arg Val Ile Ser Glu Tyr Gln Lys Leu Phe Pro
            195                 200                 205

Asp Ile Pro Ile Gly Tyr Ser Gly His Glu Thr Gly Ile Ala Ile Ser
210                 215                 220

Val Ala Ala Val Ala Leu Gly Ala Lys Val Leu Glu Arg His Ile Thr
225                 230                 235                 240

Leu Asp Lys Thr Trp Lys Gly Ser Asp His Ser Ala Ser Leu Glu Pro
                245                 250                 255

Gly Glu Leu Ala Glu Leu Val Arg Ser Val Arg Leu Val Glu Arg Ala
            260                 265                 270

Leu Gly Ser Pro Thr Lys Gln Leu Leu Pro Cys Glu Met Ala Cys Asn
            275                 280                 285

Glu Lys Leu Gly Lys Ser Val Val Ala Lys Val Lys Ile Pro Glu Gly
            290                 295                 300

Thr Ile Leu Thr Met Asp Met Leu Thr Val Lys Val Gly Glu Pro Lys
305                 310                 315                 320

Ala Tyr Pro Pro Glu Asp Ile Phe Asn Leu Val Gly Lys Lys Val Leu
                325                 330                 335

Val Thr Val Glu Glu Asp Asp Thr Ile Met Glu Glu Leu Val Asp Asn
            340                 345                 350

His Gly Lys Lys Ile Lys Ser
            355

<210> SEQ ID NO 5
<211> LENGTH: 1429
<212> TYPE: DNA
<213> ORGANISM: Homo sapiens
<220> FEATURE:
<221> NAME/KEY: CDS
<222> LOCATION: (1)..(690)

<400> SEQUENCE: 5 atg gcc ttc cca aag aag aaa ctt cag ggt ctt gtg gct gca acc atc     48
Met Ala Phe Pro Lys Lys Lys Leu Gln Gly Leu Val Ala Ala Thr Ile
 1               5                  10                  15 acg cca atg act gag aat gga gaa atc aac ttt tca gta att ggt cag     96
Thr Pro Met Thr Glu Asn Gly Glu Ile Asn Phe Ser Val Ile Gly Gln
            20                  25                  30 tat gtg gat tat ctt gtg aaa gaa cag gga gtg aag aac att ttt gtg    144
```

| | | | | | | | | | | | | |
|---|---|---|---|---|---|---|---|---|---|---|---|---|
|Tyr|Asp|Tyr|Leu|Val|Lys|Glu|Gln|Gly|Val|Lys|Asn|Ile|Phe|Val|
| |35| | | |40| | | |45| | | |

```
aat ggc aca aca gga gaa ggc ctg tcc ctg agc gtc tca gag cgt cgc      192
Asn Gly Thr Thr Gly Glu Gly Leu Ser Leu Ser Val Ser Glu Arg Arg
 50              55                  60 cag gtt gca gag gag tgg gtg aca aaa ggg aag gac aag ctg gat cag      240
Gln Val Ala Glu Glu Trp Val Thr Lys Gly Lys Asp Lys Leu Asp Gln
 65              70                  75                  80 gtg ata att cac gta gga gca ctg agc ttg aag gag tca cag gaa ctg      288
Val Ile Ile His Val Gly Ala Leu Ser Leu Lys Glu Ser Gln Glu Leu
                 85                  90                  95 gcc caa cat gca gca gaa ata gga gct gat ggc atc gct gtc att gca      336
Ala Gln His Ala Ala Glu Ile Gly Ala Asp Gly Ile Ala Val Ile Ala
            100                 105                 110 ccg ttc ttc ctc aag cca tgg acc aaa gat atc ctg att aat ttc cta      384
Pro Phe Phe Leu Lys Pro Trp Thr Lys Asp Ile Leu Ile Asn Phe Leu
        115                 120                 125 aag gaa gtg gct gct gcc gcc cct gcc ctg cca ttt tat tac tat cac      432
Lys Glu Val Ala Ala Ala Ala Pro Ala Leu Pro Phe Tyr Tyr Tyr His
    130                 135                 140 att cct gcc ttg aca ggg gta aag att cgt gct gag gag ttg ttg gat      480
Ile Pro Ala Leu Thr Gly Val Lys Ile Arg Ala Glu Glu Leu Leu Asp
145                 150                 155                 160 ggg att ctg gat aag atc ccc acc ttc caa ggg ctg aaa ttc agt gat      528
Gly Ile Leu Asp Lys Ile Pro Thr Phe Gln Gly Leu Lys Phe Ser Asp
                165                 170                 175 aca gat ctc tta gac ttc ggg caa tgt gtt gat cag aat cgc cag caa      576
Thr Asp Leu Leu Asp Phe Gly Gln Cys Val Asp Gln Asn Arg Gln Gln
            180                 185                 190 cag ttt gct ttc ctt ttt ggg gtg gat gag caa ctg ttg agt gct ctg      624
Gln Phe Ala Phe Leu Phe Gly Val Asp Glu Gln Leu Leu Ser Ala Leu
        195                 200                 205 gtg atg gga gca act gga gca gtg ggc agt ttt gta tcc aga gat tta      672
Val Met Gly Ala Thr Gly Ala Val Gly Ser Phe Val Ser Arg Asp Leu
    210                 215                 220 tca act ttg ttg tca aac taggttttgg agtgtcacag accaaagcca             720
Ser Thr Leu Leu Ser Asn
225                 230 tcatgactct ggtctctggg attccaatgg gcccacccg gcttccactg cagaaagcct     780
ccagggagtt tactgatagt gctgaagcta aactgaagag cctggatttc ctttctttca    840
ctgatttaaa ggatggaaac ttggaagctg gtagctagtg cctctctatc aaatcagggt    900
ttgcaccttg agacataatc taccttaaat agtgcatttt tttctcaggg aattttagat    960
gaacttgaat aaactctcct agcaaatgaa atctcacaat aagcattgag gtacctttg     1020 tgagccttaa aaagtcttat tttgtgaagg ggcaaaaact ctaggagtca caactctcag    1080
tcattcattt cacagatttt tttgtggaga aatttctgtt tatatggatg aaatggaatc    1140
aagaggaaaa ttgtaattga ttaattccat ctgtctttag gagctctcat tatctcggtc    1200
tctggttcct aatcctattt taaagttgtc taattttaaa ccactataat atgtcttcat    1260
tttaataaat attcatttgg aatctaggaa aactctgagc tactgcattt aggcaggcac    1320
tttaatacca aactgtaaca tgtctcaact gtatacaact caaaatacac cagctcattt    1380
ggctgctcag tctaactcta gaatggatgc ttttgaattc atttcgatg                1429
```

<210> SEQ ID NO 6
<211> LENGTH: 230
<212> TYPE: PRT

-continued

<213> ORGANISM: Homo sapiens

<400> SEQUENCE: 6

```
Met Ala Phe Pro Lys Lys Lys Leu Gln Gly Leu Val Ala Ala Thr Ile
 1               5                  10                  15

Thr Pro Met Thr Glu Asn Gly Glu Ile Asn Phe Ser Val Ile Gly Gln
            20                  25                  30

Tyr Val Asp Tyr Leu Val Lys Glu Gln Gly Val Lys Asn Ile Phe Val
        35                  40                  45

Asn Gly Thr Thr Gly Glu Gly Leu Ser Leu Ser Val Ser Glu Arg Arg
    50                  55                  60

Gln Val Ala Glu Glu Trp Val Thr Lys Gly Lys Asp Lys Leu Asp Gln
65                  70                  75                  80

Val Ile Ile His Val Gly Ala Leu Ser Leu Lys Glu Ser Gln Glu Leu
                85                  90                  95

Ala Gln His Ala Ala Glu Ile Gly Ala Asp Gly Ile Ala Val Ile Ala
            100                 105                 110

Pro Phe Phe Leu Lys Pro Trp Thr Lys Asp Ile Leu Ile Asn Phe Leu
        115                 120                 125

Lys Glu Val Ala Ala Ala Pro Ala Leu Pro Phe Tyr Tyr Tyr His
    130                 135                 140

Ile Pro Ala Leu Thr Gly Val Lys Ile Arg Ala Glu Glu Leu Leu Asp
145                 150                 155                 160

Gly Ile Leu Asp Lys Ile Pro Thr Phe Gln Gly Leu Lys Phe Ser Asp
                165                 170                 175

Thr Asp Leu Leu Asp Phe Gly Gln Cys Val Asp Gln Asn Arg Gln Gln
            180                 185                 190

Gln Phe Ala Phe Leu Phe Gly Val Asp Glu Gln Leu Leu Ser Ala Leu
        195                 200                 205

Val Met Gly Ala Thr Gly Ala Val Gly Ser Phe Val Ser Arg Asp Leu
    210                 215                 220

Ser Thr Leu Leu Ser Asn
225                 230
```